United States Patent
Rusch et al.

(10) Patent No.: US 6,500,655 B1
(45) Date of Patent: Dec. 31, 2002

(54) ISOLATED HUMAN KINASE PROTEINS, NUCLEIC ACID MOLECULES ENCODING HUMAN KINASE PROTEINS, AND USES THEREOF

(75) Inventors: Douglas Rusch, Bethseda, MD (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/849,334

(22) Filed: May 7, 2001

Related U.S. Application Data

(63) Continuation-in-part of application No. 09/773,371, filed on Feb. 1, 2001, now abandoned.

(51) Int. Cl.[7] .............................. C12N 9/12; C12N 5/00; C12N 15/00; C12N 1/20; C07H 21/04

(52) U.S. Cl. .................... 435/194; 435/320.1; 435/325; 435/252.3; 435/6; 536/23.2

(58) Field of Search .............................. 435/194, 320.1, 435/325, 252.3, 6; 536/23.2

(56) References Cited

PUBLICATIONS

Watanabe et al., Science, 271, 645–648, 1996 (see the attached alignment).*

* cited by examiner

*Primary Examiner*—M. Monshipouri
(74) *Attorney, Agent, or Firm*—Celera Genomics; Justin Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

9 Claims, 12 Drawing Sheets

```
   1 TCGCGGCCCA GGTGGTGCGG GCGGCCCTAG CCCGGCTGCG GAGCGCTGCG
  51 CGAGCGGCGG GCTGGCTGAC CCCGAGGGAC CCCCAGCGCA GCGGGTGCGG
 101 CGATGATCCT GGAGGAGAGG CCGGACGGCG CGGGCGCCGG CGAGGAGAGC
 151 CCGCGGCTGC AGATATCTAG GAGAAAACCC AGGAAAACAC GTGTGAGCTC
 201 TTTACGGGGA AGACGGGAAG GCCTGAGAGA CGTGTGTGCG TGGAGAGGGT
 251 GTCGGGTCCA CAGAGGGGAA GACCCAGTGC GTGTGCACGT TGGCCCCATG
 301 AATCCGCAGC TTCATGCAGT GGGCTGTGAC TCCCTGACGC AGATCCAGTG
 351 CGGCCAGCTG CAGAGCCGCA GGGCCCAGAT TCACCAGCAG ATTGACAAGG
 401 AGCTGCAGAT GCGGACGGGC GCTGAGAACC TCTACAGAGC CACCAGCAAC
 451 AACCGGGTGA GAGAGACGGT CGCCCTGGAG CTGAGCTACG TCAACTCCAA
 501 CCTGCAGCTG CTGAAGGAGG AGCTGGAGGA GCTCAGCGGT GGCGTGGACC
 551 CTGGCCGGCA TGGGAGCGAA GCTGTCACTG TCCCCATGAT CCCCCTGGGC
 601 CTGAAGGAGA CCAAGGAGCT GGACTGGTCT ACACCGCTGA AGGAGCTGAT
 651 CTCAGTGCAC TTTGGAGAGG ACGGCGCCTC CTACGAGGCA GAAATCAGGG
 701 AGCTGGAGGC CCTGCGGCAG GCCATGCGGA CCCCCAGCCG GAATGAGTCG
 751 GGCCTGGAGC TGCTCACAGC CTATTACAAC CAGCTGTGCT TCCTGGATGC
 801 GCGCTTCCTC ACCCCTGCCA GGAGCCTCGG GCTCTTCTTC CACTGGTACG
 851 ACTCGCTTAC TGGGGTCCCG GCCCAGCAGC GTGCCCTGGC CTTCGAGAAG
 901 GGCAGCGTTC TCTTCAACAT CGGTGCCCTC CACACGCAGA TTGGGGCGCG
 951 CCAGGACCGC TCCTGCACCG AGGGTGCCCG CCGCGCTATG GAGGCCTTCC
1001 AGAGGGCCGC TGGGGCCTTC AGCCTCCTGA GGAGAACTT CTCCCATGCG
1051 CCGAGCCCAG ACATGAGCGC TGCGTCCCTC TGCGCACTGG AGCAGCTCAT
1101 GATGGCCCAG GCCCAGGAAT GTGTGTTTGA GGGCCTCTCA CCACCTGCCT
1151 CCATGGCCCC CCAAGACTGC CTGGCCCAGC TGCGCCTGGC GCAGGAGGCC
1201 GCCCAGGTGG CAGCCGAGTA CAGGCTAGTG CACCGGACCA TGGCCCAGCC
1251 ACCCGTCCAC GACTACGTGC CTGTCTCCTG GACTGCCCTG GTGCATGTCA
1301 AGGCCGAGTA CTTCCGCTCC CTGGCCCACT ACCACGTAGC CATGGCCCTC
1351 TGCGACGGCT CCCCAGCGAC CGAGGGAGAG CTCCCCACGC ACGAGCAGGT
1401 CTTCCTGCAG CCCCCCACCT CCTCTAAGCC CCGAGGCCCT GTGCTGCCGC
1451 AGGAGCTGGA GGAGCGCAGG CAGCTTGGCA AGGCACACCT GAAGCGTGCC
1501 ATCCTGGGGC AGGAGGAGGC GCTGCGGCTG CACGCCCTGT GCCGCGTCCT
1551 GCGCGAGGTG GACCTGCTTC GGGCTGTGAT CTCCCAGACG CTGCAGCGCT
1601 CACTGGCCAA GTATGCGGAG CTCGACCGTG AGGATGACTT CTGTGAGGCT
1651 GCCGAGGCCC CGGACATCCA GCCTAAGACC CACCAGAAGC CAGAGGCCAG
1701 GATGCCACGC CTGTCCCAGG GGAAGGGGCC TGACATCTTC CATCGGCTGG
1751 GGCCCCTGTC TGTGTTCTCA GCCAAGAACC GGTGGCGGCT GGTGGGGCCC
1801 GTCCACCTGA CCCGAGGAGA GGGCGGCTTT GGCCTCACGC TTCGGGGAGA
1851 CTCGCCTGTC CTCATCGCTG CCGTCATTCC AGGGAGCCAG GCCGCGGCGG
1901 CTGGCCTGAA GGAGGGCGAC TACATTGTGT CAGTGAATGG GCAGCCATGC
1951 AGGTGGTGGA GACACGCGGA GGTGGTGACG GAGCTGAAGG CTGCGGGAGA
2001 GGCGGGCGCC AGCCTGCAGG TGGTGTCGCT GCTGCCCAGC TCTAGACTGC
2051 CCAGCTTGGG GGACCGCCGG CCCGTCCTGC TGGGCCCCAG GGGGCTTCTA
2101 AGGAGCCAGA GGGAGCATGG TTGCAAGACC CCGGCATCCA CGTGGGCCAG
2151 TCCCCGGCCC CTCCTCAACT GGAGCCGAAA GGCCCAGCAG GGCAAGACTG
2201 GAGGCTGCCC CCAGCCCTGT GCCCCAGTGA AGCCAGCTCC GCCCTCATCC
2251 TTGAAGCACC AGGGTGGCC GTGAGGGCCA GGATCCCTGC ACGCCCTCAG
2301 CCCTGGCTCC AGCTGGCAGC AAGCACCGAG CATGCCCTCC CCACCCAGAG
2351 GACCTCCGGG CAATGCCTGT CCCGCCTCAT GCTGGAGGCT GCCTCGGGCA
2401 CCTGCCTGCC CATTAAAGAC TGGTCAGACC TGTCTGAAAA AAAAAAAAA
2451 AAAAAAAAAA AAAAAAAA (SEQ ID NO:1)
```

FEATURES:
5'UTR:        1-102
Start Codon:  103
Stop Codon:   2272
3'UTR:        2275

FIGURE 1A

Homologous proteins:
Top 10 BLAST Hits

|  | Score | E |
|---|---|---|
| CRA\|18000005019652 /dataset=nraa /length=643 /altid=gi\|6680085 ... | 930 | 0.0 |
| CRA\|18000005229461 /dataset=nraa /length=718 /altid=gi\|4868350 ... | 393 | e-108 |
| CRA\|89000000195700 /dataset=nraa /length=648 /altid=gi\|7293132 ... | 309 | 7e-83 |
| CRA\|163000000492107 /dataset=nraa /length=1345 /altid=gi\|795920... | 116 | 7e-25 |
| CRA\|18000005101898 /dataset=nraa /length=775 /altid=gi\|7492978 ... | 112 | 2e-23 |
| CRA\|18000005055009 /dataset=nraa /length=861 /altid=gi\|3785952 ... | 105 | 2e-21 |
| CRA\|18000004878869 /dataset=nraa /length=882 /altid=gi\|466013 /... | 105 | 2e-21 |
| CRA\|18000005242118 /dataset=nraa /length=816 /altid=gi\|5103812 ... | 104 | 3e-21 |
| CRA\|1000682341924 /dataset=nraa /length=868 /altid=gi\|7019487 /... | 99 | 2e-19 |
| CRA\|18000005212030 /dataset=nraa /length=867 /altid=gi\|4416376 ... | 98 | 4e-19 |

BLAST dbEST hits:

| | Score | E |
|---|---|---|
| gi\|9121454 /dataset=dbest /taxon=9606... | 1207 | 0.0 |
| gi\|9344702 /dataset=dbest /taxon=960... | 922 | 0.0 |
| gi\|6702051 /dataset=dbest /taxon=9606 ... | 676 | 0.0 |
| gi\|12066980 /dataset=dbest /taxon=96... | 672 | 0.0 |
| gi\|9098957 /dataset=dbest /taxon=9606... | 672 | 0.0 |
| gi\|9202467 /dataset=dbest /taxon=960... | 650 | 0.0 |
| gi\|8008394 /dataset=dbest /taxon=960... | 628 | e-177 |
| gi\|11295927 /dataset=dbest /taxon=96... | 599 | e-168 |
| gi\|4649738 /dataset=dbest /taxon=9606 ... | 595 | e-167 |

EXPRESSION INFORMATION FOR MODULATORY USE:
library source:
Expression information from BLAST dbEST hits:
gi\|9121454   Eye retiniblastoma
gi\|9344702   Placenta choriocarcinoma
gi\|6702051   Germ cells
gi\|12066980  bocio_tumor
gi\|9098957   Pediatric pre-B cell acute lymphoblastic leukemia
gi\|9202467   Kidney 2 pooled Wilm's tumors
gi\|8008394   Uterus tumor
gi\|11295927  Brain anaplastic oligodendroma
gi\|4649738   Uterus well-differentiated endometrial adenocarcinoma Expression information from PCR-based tissue screening panels:
Human leukocyte

FIGURE 1B

```
  1 MILEERPDGA GAGEESPRLQ ISRRKPRKTR VSSLRGRREG LRDVCAWRGC
 51 RVHRGEDPVR VHVGPMNPQL HAVGCDSLTQ IQCGQLQSRR AQIHQQIDKE
101 LQMRTGAENL YRATSNNRVR ETVALELSYV NSNLQLLKEE LEELSGGVDP
151 GRHGSEAVTV PMIPLGLKET KELDWSTPLK ELISVHFGED GASYEAEIRE
201 LEALRQAMRT PSRNESGLEL LTAYYNQLCF LDARFLTPAR SLGLFFHWYD
251 SLTGVPAQQR ALAFEKGSVL FNIGALHTQI GARQDRSCTE GARRAMEAFQ
301 RAAGAFSLLR ENFSHAPSPD MSAASLCALE QLMMAQAQEC VFEGLSPPAS
351 MAPQDCLAQL RLAQEAAQVA AEYRLVHRTM AQPPVHDYVP VSWTALVHVK
401 AEYFRSLAHY HVAMALCDGS PATEGELPTH EQVFLQPPTS SKPRGPVLPQ
451 ELEERRQLGK AHLKRAILGQ EEALRLHALC RVLREVDLLR AVISQTLQRS
501 LAKYAELDRE DDFCEAAEAP DIQPKTHQKP EARMPRLSQG KGPDIFHRLG
551 PLSVFSAKNR WRLVGPVHLT RGEGGFGLTL RGDSPVLIAA VIPGSQAAAA
601 GLKEGDYIVS VNGQPCRWWR HAEVVTELKA AGEAGASLQV VSLLPSSRLP
651 SLGDRRPVLL GPRGLLRSQR EHGCKTPAST WASPRPLLNW SRKAQQGKTG
701 GCPQPCAPVK PAPPSSLKHP GWP (SEQ ID NO:2)
```

FEATURES:
Functional domains and key regions:
[1] PDOC00001 PS00001 ASN_GLYCOSYLATION
N-glycosylation site Number of matches: 3
    1    214-217 NESG
    2    312-315 NFSH
    3    689-692 NWSR

[2] PDOC00005 PS00005 PKC_PHOSPHO_SITE
Protein kinase C phosphorylation site

Number of matches: 12
    1    16-18 SPR
    2    683-685 SPR
    3    22-24 SRR
    4    88-90 SRR
    5    33-35 SLR
    6    22-24 SRR
    7    88-90 SRR
    8    440-442 SSK
    9    556-558 SAK
    10    579-581 TLR
    11    646-648 SSR
    12    668-670 SQR

[3] PDOC00006 PS00006 CK2_PHOSPHO_SITE
Casein kinase II phosphorylation site

Number of matches: 8
    1    105-108 TGAE
    2    212-215 SRNE
    3    216-219 SGLE
    4    287-290 SCTE
    5    423-426 TEGE
    6    570-573 TRGE
    7    651-654 SLGD
    8    668-671 SQRE

[4] PDOC00007 PS00007 TYR_PHOSPHO_SITE
Tyrosine kinase phosphorylation site 104-111 RTGAENLY

FIGURE 2A

[5] PDOC00008 PS00008 MYRISTYL
N-myristoylation site

```
Number of matches: 11
     1       9-14   GAGAGE
     2      84-89   GQLQSR
     3     147-152  GVDPGR
     4     166-171  GLKETK
     5     274-279  GALHTQ
     6     291-296  GARRAM
     7     419-424  GSPATE
     8     469-474  GQEEAL
     9     594-599  GSQAAA
    10     601-606  GLKEGD
    11     664-669  GLLRSQ
```

[6] PDOC00009 PS00009 AMIDATION
Amidation site

```
              35-38  RGRR
```

[7] PDOC00016 PS00016 RGD
Cell attachment sequence

```
              581-583  RGD
```

Membrane spanning structure and domains:

```
 Helix  Begin   End    Score   Certainty
   1     583    603    1.094   Certain
```

BLAST Alignment to Top Hit:
```
>CRA|18000005019652 /dataset=nraa /length=643 /altid=gi|6680085
              /def=ref|NP_032190.1| GTP-rho binding protein 1 [Mus
              musculus] /org=Mus musculus /taxon=10090
              Length = 643

Score =  930 bits (2284), Expect = 0.0
 Identities = 471/706 (66%), Positives = 520/706 (72%), Gaps = 72/706 (10%)

Query: 1    MILEERPDGAGAGEESPRLQISRRKPRKTRVSSLRGRREGLRDVCAWRGCRVHRGEDPVR 60
            MILEERPDG G GEES R
Sbjct: 1    MILEERPDGQGTGEESSR------------------------------------------ 18

Query: 61   VHVGPMNPQLHAVGCDSLTQIQCGQLQSRRAQIHQQIDKELQMRTGAENLYRATSNNRVR 120
                      P +      G  S   Q Q GQLQS RA++HQQI KEL+MRTGAENLYRATSN   VR
Sbjct: 19   ----PQDDGSIRKGYGSFVQNQPGQLQSHRARLHQQISKELRMRTGAENLYRATSNTWVR 74

Query: 121  ETVALELSYVNSNLQLLKEELEELSGGVDPGRHGSEAVTVPMIPLGLKETKELDWSTPLK 180
            ETVALELSYVNSNLQLLKEEL ELS  VD  +    E +T+PMIPLGLKETKELDW+TPLK
Sbjct: 75   ETVALELSYVNSNLQLLKEELAELSTSVDVDQPEGEGITIPMIPLGLKETKELDWATPLK 134

Query: 181  ELISVHFGEDGASYEAEIRELEALRQAMRTPSRNESGLELLTAYYNQLCFLDARFLTPAR 240
            ELIS HFGEDG S+E EI+ELE LRQA RTPSR+E+GL LL AYY+QLCFLDARF +P R
Sbjct: 135  ELISEHFGEDGTSFETEIQELEDLRQATRTPSRDEAGLDLLAAYYSQLCFLDARFFSPSR 194

Query: 241  SLGLFFHWYDSLTGVPAQQRALAFEKGSVLFNIGALHTQIGARQDRSCTEGARRAMEAFQ 300
            S GL FHWYDSLTGVPAQQRALAFEKGSVLFNIGALHTQIGARQD SCTEG   A EAFQ
Sbjct: 195  SPGLLFHWYDSLTGVPAQQRALAFEKGSVLFNIGALHTQIGARQDCSCTEGTNHAAEAFQ 254

Query: 301  RAAGAFSLLRENFSHAPSPDMSAASLCALEQLMMAQAQECVFEGLSPPASMAPQDCLAQL 360
```

FIGURE 2B

```
            RAAGAF LLRENFSHAPSPDMSAASL  LEQLM+AQAQEC+F+GL  PAS   P   C   QL
Sbjct: 255  RAAGAFRLLRENFSHAPSPDMSAASLSMLEQLMIAQAQECIFKGLLLPASATPDICPDQL 314

Query: 361  RLAQEAAQVAAEYRLVHRTMAQPPVHDYVPVSWTALVHVKAEYFRSLAHYHVAMALCDGS 420
            +LAQEAAQVA EY LVHR MAQPPV DY+P SWT L HVKAE+F +LAHYH AMALC+
Sbjct: 315  QLAQEAAQVATEYGLVHRAMAQPPVRDYLPASWTNLAHVKAEHFCALAHYHAAMALCESH 374

Query: 421  PATEGELPTHEQVFLQPPTSSKPRGPVLPQELEERRQLGKAHLKRAILGQEEALRLHALC 480
            PA +GEL    E VF QP T  +P GP LPQ  E+RR+L KAHLKRAILGQEEALRLH LC
Sbjct: 375  PA-KGELARQEHVF-QPSTPHEPLGPTLPQHPEDRRKLAKAHLKRAILGQEEALRLHTLC 432

Query: 481  RVLREVDLLRAVISQTLQRSLAKYAELDREDDFCEAAEAPDIQPKTHQKPEARMPRLSQG 540
            RVLR+VDLL+ V++Q L+RSLAKY++L+REDDF  EA EAPDIQPKTHQ  PE
Sbjct: 433  RVLRKVDLLQVVVTQALRRSLAKYSQLEREDDFFEATEAPDIQPKTHQTPE--------- 483

Query: 541  KGPDIFHRLGPLSVFSAKNRWRLVGPVHLTRGEGGFGLTLRGDSPVLIAAVIPGSQAAAA 600
                     GPLSVFS KNRW+LVGPVH+TRGEGGFG TLRGDSPVLIAAV+PG QA +A
Sbjct: 484  ---------GPLSVFSTKNRWQLVGPVHMTRGEGGFGFTLRGDSPVLIAAVVPGGQAESA 534

Query: 601  GLKEGDYIVSVNGQPCRWWRHAEVVTELKAAGEAGASLQVVSLLPSSRLPSLGDRRPVLL 660
            GLKEGDYIVSVNGQPC+WW+H EVVT+L++ GE G SLQVVSLLPS      G RR  LL
Sbjct: 535  GLKEGDYIVSVNGQPCKWWKHLEVVTQLRSMGEEGVSLQVVSLLPSPEPRGTGPRRAALL 594

Query: 661  GPRGLLRSQREHGCKTPASTWASPRPLLNWSRKAQQGKTGGCPQPC 706
                  +QRE G +TP T    P P+L WSRK +QGKTG  P PC
Sbjct: 595  W------NQRECGFETPMPTRTRPWPILGWSRKNKQGKTGSHPDPC 634 (SEQ ID NO:4)

Hmmer search results (Pfam):
Model     Description                                          Score    E-value  N
PF00595   PDZ domain (Also known as DHR or GLGF).              46.4     9e-12    1

Parsed for domains:
Model     Domain   seq-f   seq-t     hmm-f   hmm-t      score   E-value
PF00595   1/1      566     644  ..   1       79    [.   46.4    9e-12
```

FIGURE 2C

```
   1 CCACCCTGTC TCAAAAAAAA AAAAAAAGGC CAGTCACAGT GGCTCACACC
  51 TATAATCCCA ACACTTTGGG AGGCCAAGGC AGGCAGATCA CTGGAGCTCA
 101 GAAGTTCAAG ACCAGCCTGG GCAACAGGGC GAAACCCTGT CTCAATTTTT
 151 TTTTCCTTTA TAAATTACAA AAGAGAAAAC GAGCATAAAG CAGCCCCATC
 201 AGCAATTATC ACCTCATCTG CAAAAGGTCC CGGCGCTCAC TGCCGTGCCC
 251 CTCCCGCCGC TGTCCAGTTC CCTGCCTGTC ACACCAAAAT TCTCCTCTAC
 301 TTTCTCACCT CCCATCCTTT CATTTTTCCC CCTAAATTTT TAAACTTCAG
 351 AAGTGCACAA TACACATGTA ACAAACCCAC ACATGTACCT CCAAATCTAA
 401 AATAATTTAA AAAACAAAA AGGAAACTCT AAATTTTTG AGTGCAGTGA
 451 TACATTCTTG CTGTGCCAAA TCCAGTAACA CAGAAGCATG CAAAGAAAAA
 501 GGCAGCACCA CCCCCCTCCA ACACACACAC ACACACACAC ACACGCACAC
 551 ACGCACATAT GCACGCACAC ACACGCACAC GCACACGCAC ACGCACAC
 601 ACTCCAGCCT GGGCGACAAG AGCAAGACTC CATCTCAATA AATAAATAAA
 651 GAAATAGTA ATTGAATATT TTCCTTCAGG AAACAGCACC CTGCAGGGAG
 701 GGGAAGTCTT ATGACCCTCA AAGTTTGAGA GCCTCTCTTA ACTTCCCAAT
 751 GGCCTCTGTC TGCTGAACCA AGAAGCCTGC AAAACAAATA CGTAAGAACT
 801 GGATACCATT TCAGTCACAC ATGCTTGCTG ACAGTCACTG ATATGGTAAT
 851 GCCTCCTGTA CACATAGCTG ACTCTGAAGA CTGCTAAGAG GGTTTGGGTC
 901 TCTGCTGTAC AGGACCTTGG CAGCCTGCAA GGAGATGACT CACATGGAAG
 951 TCCCCACACA AGTGCACCCA GTGTGAACTT TGGAAGCATC GGCCCATGCT
1001 CAGGCCCACA GGTAAGATGG CCAGGAGCCC CTGCCCTTGA GGAAACTTGA
1051 ACCACAGAGC TGCTGGCGAA GGGGGTGGGT GAAGGTCTCA TGTAGCCTGT
1101 GTGATTCAGG CAGAAGTGAG AAGGACGGGT GGGAACCCAC CAAGTGGACG
1151 ACAAGCTGAA GGGCTCCCAG GGAGCAGACA CTTCAAGGGC CCCAAAAGGC
1201 CAGGAGAAAG AAAAAAAAAA GCCGGGTATG GTGGCTCATC CCTGTAATCC
1251 AGCACTTTTG GGAGGTTGAG GCAGATGAAT TGCTTGAGCC CAGAAGTTTG
1301 AGACCAGCCT GGGCCTGGGC AATGTGGCGA AACCCTGTCT CTACAAAATA
1351 TACAAAATT AGCCGGGTGT GGTGGTGCAA GCCTGTAGTC CCAGCTATTC
1401 AGGAGGCTGA GGTGGGAGGA TCACATGAGC CCAGGAGGTG GAGGCTGCAG
1451 TGAGCTGTGA TCGTACCACT GCACTCCGGC CTGGGGAACA GAGTGAGGCC
1501 CTGTCTCAAA AGGCCAGGAG TGGAAGACAG GCCCTAGCCA GGAGGTTTCA
1551 CGTGGCTGGC AGGGGCCTTA TGAGAAGGCT GTTGCTGGGA GGGGCCTGCT
1601 GCAGATGGCT GCGGCAGACC ACGGAGCTTA GCCTTCAGGA TTTAGATCTG
1651 GGGATGACAG GCTCCTGTGT GCTTGTTGCG GAGCCGGGAG CACAGGCACC
1701 AGAATGATCC CAGGGCTCAG CTCCAAGGCT CCGCTGGGCC TGTGGTGGGG
1751 CAGTGAACGT GGACAAGACC TGGGCTTCAG AGGAACTTGA TGACCAGGAG
1801 CCGTGGTTAC CGCCTGTGCC CTGGCCTTCC TGCTCTTCAA AGGGTGTGTT
1851 CTGAGCTGAG GCGAGACCCA CACGAAATCC GAGCGGGCTC CGGAGTCACC
1901 AGACACCTAG GGAAGTATGG AAGGCCCGGA AGGACACACA CAGCCGGGTG
1951 AGCCCCGCAG GGAGCTGTGC AGTCTCAGGT CGTCCAGTCC TGGGGCTGCA
2001 GGCCAGTTCT CCAAGCAGGT GGTCCTGGAG GCAAGCTGGT TTTGAAAGTA
2051 GGTTCTGAAA ATAGGTCAGT CCAGGAAACA AGCTCTGGAA GTAAAGAGAT
2101 TCGGAAAGCA GGTTCGTTCT GGAAACAAGT TCTACAAACA GGTAGTTCTG
2151 AAAGCACGTG GGTTCCAGAG GCAGGTGCTA GAAGGATGTG GGTTCTGTAC
2201 GGAGGTTCTG GAGGGAGGCG GGTTCTGGAC GGAGGTTCTG GAAGGAGGCG
2251 GGTTCTGGAG GCCGGTTTTG GAAGCAGGAC GACACCGACA GAGGCGCCTC
2301 GGACTGGGGC CAGGCCTGGA GCCTCCGCTC CGCGGGCAGA GAGAAGAAAG
2351 CAGGCATTGT CGGAGGACTC ACACAAGCAC TTGTCCCTAA CAAAACCGTT
2401 TTTAAAAACC CCATTGTGAA CATTTTTGGA ACAAGCCTCT TAGAGGGTCC
2451 CGTTGCCGGG GTGACAGGAC GAAACGGCGC GAGCGGGCAG ACTCCTGGAG
2501 TCCCCGCAAA GGGAGCCGAG GAGCTAGGCG CGCCGAGTCC AGGTCCGCCC
2551 TGACTCTCAG CTTGGGACGT TCCGTATAGT TTTTTTCTCC GTTTCCCGAA
2601 CTTCTCCCGC ACGCTCAGCG GCCGCCGCGG CGCATGCGCA GTACAACCTG
2651 CCAGCCAGCC GCGGGCGTTC CGGCCGCGGT TGCCAGGGGT TACCGTCCCG
2701 CGGGCGGGCG GAGCTGGCCG TCCAGAGCCC GCCTTCCTGG AACTCTGGTT
2751 GGCTGATATA GCTGTCCGTC GAAGCGGCAT TGCCGCCTAT TGGGCAATGG
2801 CCAGCTTCGC ACGCCAGACC CGTGCCCCGC CCAGCCGCGC CGCGGGCCGC
2851 CCCCACTCAG GAGGGACAGT CGGGGACCGG CGCGGGCACT CAGGAGCCCG
2901 CGGCCCAGGT GGTGCGGGCG CCCTAGCCC GGCTGCGGAG CGCTGCGCGA
2951 GCGGCGGGCT GGCTGACCCC GAGGGACCCC CAGCGCAGCG GGTGCGGCGA
3001 TGATCCTGGA GGAGAGGCCG GACGGCGCGG GCGCCGGCGA GGAGAGCCCG
3051 CGGCTGCAGG TGCGCAGAAC TGGCGCGGCG GCGGGAGGAG GGGCCCGGAA
```

FIGURE 3A

```
3101 TCCCGGCCTT TTCCTGCCCC CCCTCGAGGC GCGTTCCGGG CGCCCCCCTC
3151 CTACGTACTC ATTCGGCCCG GACGCAGGCA GGGAAACTGA GGCCAGAGCC
3201 TGCGTGCCCT CCTCCTCTGA GCTCGGTGGA GGTGCTTCCA GGCCACTCAT
3251 GTGAGCCGGG AAATGCGGAC AGCCAAAGTC TGGATCATCC TCACCGCTGA
3301 AGCGGGTTGG GGGGACGCCC TCCTCGTGTC CCCCTTCTGG GCGGATGTGG
3351 GGCTGGGATC TGTGAGCGCC CTCCCCACAC CCGCCATCGT GTTCCTTTCC
3401 GGCACCTGTA CAGCCTCCTT CCCTAGTTCG GTCCTCCCTC TGCATCCGCT
3451 CAGGAACTGC ATGCCCATTG GGTGCACTGG TAGCAGCGGG CAGCGAAGCC
3501 TCCTGGGTAT GGGAAACCGA GAGAGGTCTT CCCGGCTGGC CTCTTCTCAC
3551 TTCCCAAACC TCCTTCCCTT CTGAAGTCCC TAACCCGGGG TGCTGACTGG
3601 GCAAGTGGGA GGGGTGGGCA GGGCTGTGGA GACCTGCTGA GTCTGTGCCT
3651 GGGAAGGAGG GGACGTCTGT GGGCCTTGCT CTGCAGCCCA GAGCCTGCTT
3701 GTTCCCTGCG GACCAGCTCG AGGCTGCCCC AGTCCTCCTG CCAGGCCCTG
3751 GGCGCCCACG CCCGCCACGG GCTTTCAGCC GCGGGCTGCT CCTGCTCCTC
3801 GCCCCGGGTG AGCCTTTGAT AGCGCGCGGC CCTCCTCCCC TCTGGGACGT
3851 CAGACTGTGT TGTCCCTGGG CTGGTTCTAC TCGGCTTTGG TGTTTGGGGT
3901 TAGGTCTCCT AGAGGAGGAG GCGGTGCTAT CAGCCAGGGT TTGGCTTCAG
3951 GTCACTGGGC TGGTGATGCT GACCGTAGCC CTCAAGGTCG CCCTTCTTGC
4001 CCACCCCGAG GCGTGCCAGA GGCTGCAGCA CCTCCTGGGC ACTGGAGGGA
4051 AAGAGGCAGC CTGTGCCTGC CCCCTGTGAA CTTGCTCTGT CAGGGCGGCC
4101 ATGCCTGCAG GTGGCCTGGG ACGGCACATG TTGTTTTGGG TGGAATGTTT
4151 GGGAGGCTGT ACAAACAAGA TGTCCCAGAG GGCTCCGGAG GTGACGCTTT
4201 TCAGGCTGGG GGCTGTGCCT GGGCTCCCTG TCCTGGCCCT CCCTGGGCTG
4251 CCACCTTGGA AAGTTGGGGA GAAGCTGTTT CCAGGCTGCC GTGTCTCTCA
4301 CAGCGTCCAG AAATGACCCC ACAGTCAGGG TACTGGGGAG GGGCCCGTGG
4351 GAGGTGGCAG TGGGCGGAG GCAGGCCCTG TGTCACACGC GCACCACTCA
4401 GGCTGTCCTG CCATCTGGAA AGTCTTCCCC GATGCCTGCT GCCGGGCTAG
4451 AGTGAGGCCT GTTCCACCCC CATCAGGCTG GCCCCCAAAC TGGCCCTAAA
4501 GCTCAGAGTT CAGTGGGTCA GGGGTCGGTC GTTCATCCAC TTAGAGGCCA
4551 CACCTGGGCC TGAGGCCCTG TGGACAGGTC TGGGTGACTT GTATTTGCCC
4601 CAGGCGTGAT GAGAGCAGGC TTCAGCAAG CGCTTACCTG GTGCCAGGGC
4651 CAGTGCTACA GCTGGAGTCC TGCCATTGGT GCCTCCCAAG CCCTGGGCCT
4701 CAGCCCGTCT GATGAACAGG GTGAGTAAGT GGCCAAGGCT GCCAAGCTGG
4751 GAAGGGGAGA AGCCTGGCAC GGCCCAGGGT GGCCAACCCA GCTGCCGTCC
4801 CTCCCGCAGG GGCTGCAGGG GCTCCCGGGG GAGGACCACA AGGAATACAG
4851 CCTGGCTGTA TGCAGAAGGT TCTGTGGTTT CCTGGGGAGG CCAGTGGGAG
4901 AAGGGGGAGC AGGCTGCAGA GGGAGAGCGT TGGAGCAGCA GGTGGGCAGG
4951 GTGGCTGTGC CCCCCTCACC TGGTCTCCAG CATGCCGAGT GGGTCAGCCT
5001 GAGGTTCCCC AGCCTGGCTG GACAGGAGCA CCCTCTGGGT GCTGGTTACA
5051 GGTTCCCAGG CCCCTGCCCA GGTAGATTGG GCTCCAGGAA GAGGGGTGCT
5101 CAGGAAGCAC CAGTGCCTGG GTACCCCAGG GAGCATCAGA GAGAGTGGGA
5151 GTCCCTGCCG TGAGTGGCCA GTCTATGATT CCTCTGGCGT GCGTGCTGCT
5201 TATAGCCCTG TGTCCCAGGA GACACCTGTG CAGCAATGCC CTTTGAATTC
5251 TGTTCCCTCA TCAGTGGGGG GCAGAGATGG TGGGTCAGGT GGGTGCTGGG
5301 CTTCCACCCT CCTGGGGCTT CCAGTTCTTG CATTCAGGTG AGACTTCAGT
5351 GGGGGCAGAG GAGAGGGGTA CCTGAGATGG GTGGCTGTCA GCATACAGGG
5401 TGCCCAGGGC CAGGGCTCTG AAGGGAAAAA GCTGGTTTGC TCCAGGTGGG
5451 TGACCTCTCC CTGGGGACTG CCTGGCCCAG GCCAGGGGA TCCTGGGGGA
5501 GAGTGGAGGT CTGGCCCTGC TCTGATGTTT TGCTGTTCCC AGACCTGGGC
5551 TGGGATAACT ATCTCTGCCT TTTGCCCGTC CCCAGGTCAG CCCCACTCTG
5601 GCCAGGGCCA CACTGTTTCC TCCTGGGCAG AGGAGCCCCA GTGTCAGGGT
5651 TGGGGGGCTG TTTCTCTGTT CTTCGTCCCT CTCCATCGAG GCATGGCCAG
5701 GCCCTTCATG TGTGGCTGCC TCTCGGGACC CCCACAGACC ACAGCCTCTC
5751 TGTCCTTTCC TAATGCAAGG CGGAAATGGC CACAGTGGGG TGTCAGGGCA
5801 CCGTGGACGT GGGGGTGGGG AGCTCCAGGT CACCTTTGTC TCCAGAGGGT
5851 GGGGAGGTTG TAGCAGGAGT AGGGGCCTGA ACGCCTGTGT CTATGCCCCT
5901 TCCACTGGGC TCAACCTTCA ACCCAGTGTG GAAAGTGGGG CATGGGCCGC
5951 CCACCTCCAA GGTCTACCCA GCCTCAAAGG TCCGGCTCGG GTCTGCTCCT
6001 CCGCCTGTAG GCCGGGAAGT CACTTGGCCT GCAGGGAGCA CTGCGGGTAG
6051 GGAGGCCGAG GAATGGACCA GGCCCACAGC AGGTGCCTGT GGGGCTCCAA
6101 GGGGCCAGGC TCCCCGCAGC TCTCCTGGGG CCAGGAGGGG AGCAGGGACC
6151 TGGCTGGGTG TCTGATGCCC GTCGCACAGC CAGAGCCCTT AAAGCTGCTG
```

FIGURE 3B

```
6201 GAGCCTTGCA GCGGGGCCTT TGCGGGGAGG GGGTGTAGCT GCGGTGGGTG
6251 GCACGGGGGT CTCCTAGGTA CTGGGCAGAG GCCCTCGAGG TGGTAGCGCC
6301 GGTGGGAAAG GTAGGGATGG GAGGCGGGGG TGGGCGGGCC TCAGGTTCAG
6351 GGAGCTTCTC AGATCTGAGG CGCCCATGCC CCTCTCCCAC CTGTGGGCCT
6401 CTCCAGCCCG AGTCCCTGAA GCAGCTCTGG AGGTAATTTC TTTTCTGGAG
6451 GAGGCGGGAG TGAGAAACGG GAGCAGGGTG AGGGTTCCCA AGTGCACATC
6501 GGCCCGTCCG CTGCTGGGTG GTGTCCACGG GGGCAGGGCT GGGCTGGGGG
6551 AGGCCAGGGT CCTGGGCCGG CACACCCTCC TTCCGGCTGC CTGTGTCCCT
6601 CCCTCCAGCT GCCTGTGTCC ATCCCTCCGG CCGCCTGTGT CCCTCCCTCC
6651 GGCCCCTAAG CGCCAACTCA TCTTCAGTTC AGGGACCTCC GTCAGGCTCC
6701 CTCACCCCAG CACTCAGCAG GAGGCTGCCG GCCTGGGTGT CCAGGGGATG
6751 GTGCGGGTGT CCAGCAGACA GTACAGGGGT TTGGGGGATG GTACAGGTGT
6801 CTGGGGGATG GCGTGGGTGT CCAGCAGATG GCGCAGGGGT TTGGGGGATG
6851 GCACAGGTGT CTGGGGGACA ATGCGGGGGT TTGGGGGATG GCGTGGGTTC
6901 CAGGGGATGG TGCAGGGGCT TGGGGGATGG TGTGGGTTCC AGGGGACCGT
6951 GTGGGGGTTT GGGGATGGCG TGGGTTCCAG GGGATGGTGC AGGGGCTTGG
7001 GGGATGGTGT GGGTTCCAGG GGACGGTGCG GGGGCTTGGG GATGGCGTGG
7051 GTTCCAGGGG ACGGTGTGGG GGTTTGGGGA TGGCGTGGGT TCCAGGGGAC
7101 GGTGCCTCAT CCTCCAGTCT CTGTCTCTGC CTTCCCATGG CCACCTCCAT
7151 GTGACTGTGT TCAAATTCCC CACCTCGTAT AAGGACCCTT GTCACTGCGA
7201 TTAAGGACCC CCTACTCCAG GGTGGCCTCA TCTTAACTCA TTATATCTGC
7251 AAAGACCCTA TTTCTAGAAA AATTGCAGTC ACAGGTACTG GGAGTCAGGA
7301 CTTGAACCTG TCTTTTGTGG GGACACAATT CACCCATAAT AGATGGTCAC
7351 CCGCTCAGCT GGCTGCTGTG ATTTTGGGGG GCTGGACGAG CAGGCCTTCT
7401 GTCTAGGAAA TCAAACCTTT CTTGTATAAT GGGAATAAAC TAATTAAAAT
7451 GCACACAAAG ATCTCGTTCA CATTAGCAAA AAGAACTCTC TCCAGATATC
7501 TAGGAGAAAA CCCAGGAAAA CACGTGTGAG CTCTTTACGG GGAAGACGGG
7551 AAGGCCTGAG AGACGTGTGT GCGTGGAGAG GGTGTCGGGT CCACAGAGGG
7601 GAAGACCCAG TGCGTGTGCA CGTTGGCCCC ATGAATCCGC AGCTTCATGC
7651 AGTGGTAGGT CAGTTTCATG GTGGCAAGAT TCACCTTCAG ACGCCACAAG
7701 GTCCTGGGGA AGAAGAGGTC CTGTCTCCCG ACAAGGGCGG GAAGCAGTCC
7751 CAGGAGCCAC CAGAGGCCTT GTCTTGCTGC TGACTGGCAG AAATGGCCAG
7801 GTTGGCCACG CCTGACTCAG ACCAGGCTCG CCCCAGGGCT GGGTGGGAGT
7851 CAGTGTCCCT GAGCAGTGAG CCCTGAGCAG CACTGTGGGT CTCAAAGCAT
7901 GGAAGGAGTG GGTGCTGGAG AGGCAAGCCA GCCAGCCCAC GCCTGGGAGC
7951 CCACCCAGGG GACAGCCACA GGTAGCTGCA AATAATCTTG TCCGGGTGGA
8001 GACCCAGGCA TTCCCACATG GCCACGGGGA AGAGTGGGGG TTGGGAGGCC
8051 ATGGTGAGAG GGAGGGACAC GTGAGGATCA TGTGGGCAGG ACCCCAACAC
8101 CACAAGGGTG GGGTGGGCTG AGGCATGAAA CTGGATCTCC CTAGAGTGAA
8151 ATGTAAGCTC CAGCACGCTG GCACCACTGA CGACACAGGA GCCATCAAAG
8201 TCCAGAAGGG GCCCCGACTG GCACGCCCCA CTCTTTCGCC ATGGCTGGTG
8251 CTGGGCAGGG CCGCGGGGCT GCAGTCTGGG TGCAAGGCTC AGAGTCATTT
8301 CTCTGTGGAT AGGGAGGGCA CGGGTGTGCG TTCGCTTCGA GAACCATTCC
8351 CAAAGTCAGA CCGCAGCCTC TGCACCAACC ATCGGGGGCC AGTGGCCGCC
8401 CCCAGAGCCT CAGGGACCCT GTCCTTTGAG CCCACGCCTA AACCCACATG
8451 GGAATGATTT GGAGGCGTGG GTGAGTTGGA TGGGAAAAAA ATTGGGAGGG
8501 GCAAGGGGGG GATCCAGAAT GAAATCCAGA AGCGCAGAAG GAAGGCTGTG
8551 AGGAGCAGTG GGCCGCCTCC TGCAGGGCTC CCGGAGCCCC TACTTGTCCA
8601 GGCTGCCTGG TGAGACCCTG GCTTCTGGTG TCCTTGGCAG GTGCCAGCCT
8651 CCCCCGCTGA CCCCCATCAC GAGTCAGCAG CTTACCCCAC CGACCACGTC
8701 CTTCTGCATT GACTGCCTCC TGTCCTGCTC TGGCCAGGCC TGTGTTCACA
8751 CTAGTTCTGT CCAGCCCCTC CCTGTGAGGC CAGCTCCAGC CCCAGCGCAT
8801 GGTGACCATC CCGTTACCCA TGGGCAGGAT GCACTCCTCT CAGTGGCTGG
8851 CGAGGCGCAG CCTGGTGCGG GCGCCACGGG GTCGGGCTGT GATCGCCTGT
8901 GGCCTCCCTG CAGGGCTGTG ACTCCCTGAC GCAGATCCAG TGCGGCCAGC
8951 TGCAGAGCCG CAGGGCCCAG ATTCACCAGC AGATTGACAA GGAGCTGCAG
9001 ATGCGGACGG GCGCTGAGAA CCTCTACAGG TCAGTGCTTG AGACTGCCCG
9051 GCCCCGGGAG CAGGGCCCAC CTGGGTGAGG GGGCAGGAC AGCCACGCAG
9101 GCAGATGTCT GCCCCATGGC CGGGTCACAG AGACAGGTGC ATGAGCAGCT
9151 GGGTCCTGGT GGGCACGTAG TACACGTGAT GCTCAGCCAT GACCCTCACA
9201 GACCTGCCTC CGTGGGCCTC TGTGCTGGGC TGGAGGTGCC AGGAAACCAG
9251 TGTCCCTGCC GGGTGTGCAG CTTGGGAAGC CCCAACAGTG CACGTGGGGG
```

FIGURE 3C

```
 9301 CTTCTCAGAA GAGGCATGGT TGAGGCTGAG CTGTGGCAGG TGACGGCGCG
 9351 TCCCAAGGTT GGGGACCTGG GAGGGGGTGG AAGACCTGGG CTGCCTCTTC
 9401 CTTAGAGCAC ACCGCCTGTG TGCCACACAT GTGCGTGTGA GTGCCCCTCG
 9451 GTCCCCTTAG CACCTGCTAC CTCGCTGCCC CCATCCTGGC CTTCCCTGGG
 9501 GACCTCCGGT CCCTTTGCCA GGCCCTGATG CAGGCACAGA GAGGTGTGTG
 9551 GCTCTCACCC ACCATCCAAG GAGTGATGTT TGAGTGCTGT CGAGGGCTGT
 9601 ATGAGCCCCA AGAAAGCCG TGGTGCTGAG GGAGGTGCCC CCAGGCCAGA
 9651 GTCGGAACAT GCAGGTGCTG GGTCGGGGT GATGAACTGT AGGGGGCATC
 9701 ACCTGTGAGC CCCCGGATCC CACTGCTGCC CCTGCCCCAC CCATGGGGGG
 9751 CAGACCCTGT CAGCGACGTC CTCTGCAGGG TGGGCTTGGA GCTTTGACAG
 9801 GTCAGCTGGC AGGACGGCTG CAGTGGGCAC GGGGCCTTTG GCTCTGCCTT
 9851 GGGGCTGGGC TTTCAACTGC CGCGGCCTCC CTCAGAGCCA CCAGCAACAA
 9901 CCGGGTGAGA GAGACGGTCG CCCTGGAGCT GAGCTACGTC AACTCCAACC
 9951 TGCAGCTGCT GAAGGAGGAG CTGGAGGAGC TCAGCGGTGG CGTGGACCCT
10001 GGCCGGCATG GGAGGTGCGG GTGGGGCCG GGACAGCACG TGCGTGTATG
10051 TGTGTGCACG TGTGCGTGTG TGTGTGCATG TGTGTGCACG CATGTGTGTC
10101 TCTGTGTGTA TATGTGTGCA TTGTCTGTGT GTGTGCGTGT GTGCATGTGT
10151 GTGCATGCAT GTCTGTGCGC GTGTGTCTGT GTGCATGTGT CTGTGCATCT
10201 CTGTGTGTGT GCGTGTGTCT CTGTGTGTAT ATGTGTGCAT TGTGTGTGTG
10251 CATGTGTGTG TGCATGCGTC TGTGTGCGCG TGTGTCTGTG TGTCTGCATG
10301 TGTCTGTGTG TGCATCTCTG TGCGTGTGTC TGTGTGCACG TGTCTGCGTG
10351 CGTGTGCATG TCTGCGTGTA TGTGGGTGTG TGTTTGCCTC TATGTGTGCG
10401 TGTATGCACG TGTGTCTGTG TGTGTCTGTG TGTGCGTGTG TGTGTGTGTC
10451 TGCACGTGTG TGCATATATG TGTGTGCGTG CGCATGTGTG TCTGCATGTG
10501 TATGCACGCA TGTGTTTGTG TGTGTGTGTG CGCGTGCATG TGTGTGTCTC
10551 TGTGTGTGTG TGTTTGCTTT TGGGCGGTT TAGGACGGTG GGGGTGGTG
10601 CACAGGTGCA AGGATGCCCC CCAGGACACA GGCGCACGTG CACACCCATG
10651 AGGGAGGGAG GCACCCTGTG CCACAGAGCC CTAGGAGTGG ACCCCGGGCT
10701 GCCGTGGGCA GCAGGGTTTG GCCTTACAGT CTGAAGTCGA TGCTTCTGGT
10751 TACAGCGAAG CTGTCACTGT CCCCATGATC CCCCTGGGCC TGAAGGAGAC
10801 CAAGGAGCTG GACTGGTCTA CACCGCTGAA GGTAGGTACT GGCCTCCAAG
10851 CTCTGAGATA CACGGCCCTG CCCTGGGACC AAGGGGGTCT TGGAGGCTTT
10901 CTGGTCCAGC TGTCTGGTTG AACAGATAGG GAAACTGAGG CCCAGAGGGA
10951 GGGAGGCTTA AAAGGGACGC AAGGGACCTG GCAGAAATGG CCACAGGGAC
11001 CCAGCCTCTG CTGCGTTCAG GGCCCCGCTG GTGCCTGCGC CCCAGGCCGG
11051 GGCTGATCCC ATAGAGTGGG TGTGAACATG TGCCCTACCC TCGGATGGGC
11101 AATGCCCTAG GAGGATGGGG CCTGGAAGCC CCAGCCGGAG CACAGGGTAC
11151 AGGCTCGCCC ATGGAGGGCA CCACTGGCTT GGGGCCACAC ACCCAGCACT
11201 GGCTCACGAG GGTCCTGGGG AGAGCTAGAA CAGACTGGCA CTGCCTGGCA
11251 GGGCCCCACG GGAGCCACTG ACTGTGTTCC GTGTCCGAGT CACTGAGTGG
11301 CAGATGGCAC CTGCCTCCCG GCCACGGGGA TGAATAAGGA AACGCACGTA
11351 AAAGTAGCGC TGAGTCTCCA GGCCCCGCTT CTGTGATGGG GTGGGGAAAC
11401 CCCAGGGCCA CAGGGGCTCC GACCCGCATC AACCCACCAG GCCCCTCCAT
11451 ACACATTGGC CCCCAGCCCT TCTCTGGGGC TTCCACTGAG GGGCCCAGGG
11501 CCCCCACGCT GCATGGCAGC CAGCCTGCTC TGCGGCACAG ACCCTCCCTC
11551 CACCATGAGT CTTTTCCCAA GGTGGGTTGG GAGACCTCAG GGAAGGAGGC
11601 CAGGCACAGG GGTACTGTGG ATGCCAACAC CTGCCCCCA TCAGGAGCTG
11651 ATCTCAGTGC ACTTTGGAGA GGACGGCGCC TCCTACGAGG CAGAAATCAG
11701 GGAGCTGGAG GCCCTGCGGC AGGTGTGTGG TTCCCCCGCC CACCCACCCT
11751 CCTGCAGCCC TGGGAGACAC ATGCAGAGGC TGAAGCTGAA GTCAGGAACA
11801 GACAGAGGAG CTCAGCGTAG ACATCTCGAG GACGTGGGGA GACGGGCGCA
11851 CCAGGGGCCC TGTGTGTCCA GACCCAGCCA GGGGGCGTGG AGGGGCTCCC
11901 AGGTGGCTCC GGTGCCGCAT GCTGCTGGCC TTCGGGAGTC ACGGCTGCCC
11951 AGGGCCCCAC TGGCTTTGCC TCCCGCCCC CCATGGTGCT GGTGCCCATG
12001 GGACTTCCCA GGGCAGTGTG TGTGAGTGGG GTGGGCCAGG GCGGTGGGGC
12051 CCAGTGGCTC CTGCCCTGCA GGCCATGCGG ACCCCAGCC GGAATGAGTC
12101 GGGCCTGGAG CTGCTCACAG CCTATTACAA CCAGCTGTGC TTCCTGGATG
12151 CGCGCTTCCT CACCCCTGCC AGGAGCCTCG GGCTCTTCTT CCACTGGTAG
12201 GGGCTCTGCG GCGGAGGCA CCCTGGGGAG GGGAGGCCCA GCTGCGGGAA
12251 CCGTGGGAAC TCCACCCAGC CTGACCCAAC ACTGCAGGTA CGACTCGCTT
12301 ACTGGGGTCC CGGCCCAGCA GCGTGCCCTG GCCTTCGAGA AGGGCAGCGT
12351 TCTCTTCAAC ATCGGTGCCC TCCACACGCA GATTGGGGCG CGCCAGGACC
```

FIGURE 3D

```
12401 GCTCCTGCAC CGAGGGTGCC CGCCGCGCTA TGGAGGCCTT CCAGAGGGCC
12451 GCTGGTGAGG GCGGCCCGGG CCGCGGTGGG GCACGGCGCG GTGCCAGGGT
12501 GTTGCAGAGC CCCTTTTGCA GGGCAGGAGC TGGGGAGTGG TTAGGACATC
12551 AGTCCCTCAG GTAGGGGGAG TGAGCACATC AGGTCCATAT GTGTCCCAGG
12601 AGCATCCCTA GCTGGCCGCC CTGAGTGCTG CATGGGGCAG AGATGGGCAG
12651 GTACAGGGCC CTGCCTGTGT GAGCACCCCT CCCTCCGCAG GGGCCTTCAG
12701 CCTCCTGAGG GAGAACTTCT CCCATGCGCC GAGCCCAGAC ATGAGCGCTG
12751 CGTCCCTCTG CGCACTGGAG CAGCTCATGA TGGCCCAGGC CCAGGAATGT
12801 GTGTTTGAGG GCCTCTCACC ACCTGCCTCC ATGGCCCCCC AAGACTGCCT
12851 GGCCCAGCTG CGCCTGGCGC AGGAGGCCGC CCAGGTGAGC TCGGGCACCC
12901 GTGTCAGGAT GCAGGGGGTG GGGCCGAGCT GGGGTCAGAG CCCAGGTCCA
12951 GGCATGCGTG AGCTCTCCCA CCTCCTTCCT TGTGTGTCAG CCCCGAGCCA
13001 GCTGTTGTCC TGCTCCCTGG GGGGGCTGGT CAGGAACCTG GGGACCCGAG
13051 CCTCTGCCTC CAGGGGATGG CACAAAGCAG CAGGAACTGA GGTGCCAGGG
13101 AGGCTGCTGG GATGGTGGTC GGAGCAGGTG GAGGCTGGGT AGGGAGAAGC
13151 AGGCACCACC TGGAGAGTGG GAGGCCCTCG CGTGCCTGCC ACATCCACCG
13201 GCAGGTGGCA GCCGAGTACA GGCTAGTGCA CCGGACCATG GCCCAGCCAC
13251 CCGTCCACGA CTACGTGCCT GTCTCCTGGA CTGCCCTGGT GCATGTCAAG
13301 GCCGAGTACT TCCGCTCCCT GGCCCACTAC CACGTAGCCA TGGCCCTCTG
13351 CGACGGCTCC CGTGAGTGCC CACCGCACTT GCCCATGGTA CTGCCAAGGC
13401 CCCCCCGCGC AGGGCTCACA GCCTCTCTGT CCCCCAGCAG CGACCGAGGG
13451 AGAGCTCCCC ACGCACGAGC AGGTCTTCCT GCAGCCCCCC ACCTCCTCTA
13501 AGCCCCGAGG CCCTGTGCTG CCGCAGGAGC TGGAGGAGCG CAGGCAGCTT
13551 GGTAAGGCGC CCATGGGTGG AGTGCCCTGG GGCTCAGATG GTCACCAACG
13601 GTGGCAGGGT GTCCCCCACC ACCCTCATGC TGTTTGCCAC CTGCTGTCCC
13651 CGTGCTGACG AGTTGGGCCA CCTACCTATC CCTGGATGGC CTGTGCCTGA
13701 TGGGTGACGG CCCAGCGCAG GGGCCCCAGG AGTGCTGGGC AGCCTCTGAG
13751 CAGGTGGGAG ACCACTGGGA GCAGCTCATC CCTGGCCCCT GCTTTGCACG
13801 TGGCAGAGCC CTCCTGCACA GCCAGCTCCT CACCCCGTG GCGCGCACCC
13851 CCAACGAAAG TGGCTGTGAT GAGCCCCACA GCCCTGGCGT TGCCCACTCC
13901 TTCTGCCACG TCCCAGGGCC CACGGGCCCA CATGGTGTGT GACATCCCAG
13951 TGCCCCGCGT GCAGGCAAGG CACACCTGAA GCGTGCCATC CTGGGGCAGG
14001 AGGAGGCGCT GCGGCTGCAC GCCCTGTGCC GCGTCCTGCG CGAGGTGGAC
14051 CTGCTTCGGG CTGTGATCTC CCAGACGCTG CAGCGCTCAC TGGCCAAGTA
14101 TGCGGAGCTC GACCGTGAGG ATGACTTCTG TGAGGCTGCC GAGGCCCCGG
14151 ACATCCAGCG TGAGCAGCCA GGGCCTGTCT GGGTGGCTGC ATCCCTGGCC
14201 AGGGTGGGGG CCTTCGTCCT GGAGAAAGGG AGGCTGATTG CATTAAAGAT
14251 GCAGTCACCA CGATGAATTA AACAGCAGTA GCACTTTCCA GGCCACGATC
14301 ACAGGGACCC ACAGAGCTGC TGGGCCCTTC AGGGGCCTGG GGGATGACCA
14351 CGCTCCTCAG CACCTCCCTC CCTGCACTGG CCTCCTACCC TGAGGGGAAG
14401 CCCACAGACC CAGGACAGGC ATGGCTGGGA CTTCAGGGAG GGATTTTGGG
14451 AGCCACTTGG GGCAGAGGGG GCTGTGTGTT CAGGGCACAC CTGGGGCAGC
14501 TCCTCCCACC ATTGCAGAGT GGCCAGGCCT GGAGGTCAGA AGCGGGCCT
14551 GTGTGCACTC AGGGTCATGC CCTGCGCCCT GGAAAATCCC CGAGGCAGGT
14601 CTCCACAGTC TCCCAGCTTA GCTCTGCTCT TACACCCTCT CAGCTAAGAC
14651 CCACCAGAAG CCAGAGGCCA GGATGCCACG CCTGTCCCAG GGGAAGGGC
14701 CTGACATCTT CCATCGGCTG GTGAGCACAC CCGTCCCCAG GCACCGCCCA
14751 GCATGGGCAG CTTGGGCTGT GTGGCTCTGA CCAGCACATG GCCTCAGACA
14801 GGCCATTGAT GGTGGTCCAG CCCTCCCCAC CCACCTTGTG GAACCCCACG
14851 GTGTCCCTCG GTGCACAGGT TGGATGGATG TGCTAGTCAG GTGGGGTCTC
14901 CTCAGTGTGT GGCCCAGCTG GGCCTCTGAC CTCTGAGCCC CTGCCAGGGG
14951 CCCCTGTCTG TGTTCTCAGC CAAGAACCGG TGGCGGCTGG TGGGGCCCGT
15001 CCACCTGACC CGAGGAGAGG GCGGCTTTGG CCTCACGCTT CGGGGAGACT
15051 CGCCTGTCCT CATCGCTGCC GTCATTCCAG GGAGCCAGGC CGCGGTAAGG
15101 GCCCCGCCGG CCCCCTGAGG CTGAGTCCTT GGTGCCAGCC AGGGTGTCCT
15151 GTCCCCACCT CACCGTCCAA GTCTCCCCAC AGGCGGCTGG CCTGAAGGAG
15201 GGCGACTACA TTGTGTCAGT GAATGGGCAG CCATGCAGGT GGTGGAGACA
15251 CGCGGAGGTG GTGACGGAGC TGAAGGCTGC GGGAGAGGCG GGCGCCAGCC
15301 TGCAGGTGGT GTCGCTGCTG CCCAGCTCTA GACTGCCCAG CTTGGTGAGC
15351 CCCTGGGGCC CCAGAGGGGC GGTCCCCAGC TTGCTGTCAC CACCCTGGCC
15401 CTGGGCCTGC CTTGGATGCT TGAGCAACAT TGGAAGGGG AGGTGGGGCT
15451 GCAGGTAACC CTCCCTGGGC CGCCTCCTGG GCAGGGGCCA CCTGTGCTGT
```

FIGURE 3E

```
15501 GGCCTCCATC TGGCAGCTCT TGCCCTGACC CCGAGGATGC TGCAGCCCAC
15551 CCCTCACTGG GCCTCTGTAT CCTCAGACTG GAGGCTTCTG GGCCAGGCGC
15601 TCCATCCCAG AGGTTTTCTC TACCCAGCAT GGCTGACCCA GGGTTGGGTG
15651 AAACCCATGG GCCCCTGCTA TGTGGCCACC CTGATGGGAG CCCCCAAACA
15701 AGCCCCCGAC GTGCCAGCCC CTCCCAGGTG GTTCTCACCC CTCCCAGACT
15751 GGCTGCAGGT GGGGACAGGC CAGCAGTGGC TGACCACAGT CTGTCTCTGT
15801 CCCTGCTGCA GGGGACCGC CGGCCCGTCC TGCTGGGCCC CAGGGGGCTT
15851 CTAAGGAGCC AGAGGGAGCA TGGTTGCAAG ACCCCGGCAT CCACGTGGGC
15901 CAGTCCCCGG CCCCTCCTCA ACTGGAGCCG AAAGGCCCAG CAGGGCAAGA
15951 CTGGAGGCTG CCCCCAGCCC TGTGCCCCAG TGAAGCCAGC TCCGCCCTCA
16001 TCCTTGAAGC ACCCAGGGTG GCCGTGAGGG CCAGGATCCC TGCACGCCTC
16051 AGCCCTGGCT CCAGCTGGCA GCAAGCACCG AGCATGCCCT CCCCACCCAG
16101 AGGACCTCCG GGCAATGCCT GTCCCGCCTC ATGCTGGAGG CTGCCTCGGG
16151 CACCTGCCTG CCCATTAAAG ACTGGTCAGA CCTGTCTGAG CCCAGTGATG
16201 GGAGCTGTGG CCTCTTCACC CACACACAGA AGGATGCCAG TCCCTCTGTC
16251 GGTCTGAGGT CAGCTTCCTG GGGCTGCCCC ACCCTGAGGG CTCCTTACAG
16301 GGTGCTCCTC ACAGCCATCC CATCTGTACC CCCGGGCTCT GTCCACCCTG
16351 CTGCTGCCCT GGGCACAGAC CCTGAGGTCT CAGTCCTGCC TCCAGCCAAG
16401 TTTCTGCCTG GTGCCCAGTG ATTCCTGCTG GGCACCCCTT CGCTCACTGC
16451 CCCTCCACCA TGCAGCAGCC AGACACACCC ACAGCACCCG AAGACCTCTA
16501 GGCCGGGTCC CAGACATGGC CTTCCCCCAA AATACTTCCT GCTGTCCTGT
16551 CTGTGCACAG AGCAAGGGAC TCCCCACCTC TGCGCCCTGT GCTGGTCATC
16601 ATGGGCTCTG TGCTGGTCAA CCCAGCAAGT GTCCGTTTG CCCAGGAGTC
16651 CCTGGTGTCG TGGCCCAGGT CTCATGGTGG CCCTAAGCCT GCCAGCCCTG
16701 CTGCCCGCCT TGCTGTCCTG CTCTGAGCAT GGGTGCCACC CTCCAGCTCC
16751 TGGGCGTGTC ACTTCTCTCT GAGCCTGGGG CCTGCATGGG CCCCCAGCCC
16801 TCCCCAGCCT GCTTGGGCCG CTCCTGCTGG CCTCCACAGG CCGTGAGCTG
16851 TCAGTGTCTC AAGCAGGGGA AGTGAGGGCT GCCTCCAGGC CTCCGTGTAC
16901 TGGGTGGACA ATGGCCCCCA AAGGCCGTCG GCAAGAACAC CACCTCCAGG
16951 ACCCCTACAG CAGTGGGCTC AGGACTTGGG CACCAAGAGG AGAGGGTGGG
17001 AAGGGCTGCA GAGTCAGGGC TGCACCCAAG AGGAGCCACG GAGCCGGAGC
17051 CGGAGCGGAG GCCCCCACCG AGGGCCCAG GGCCTGGCAG GTTCCGGAAG
17101 AGACAGGGCC AGCGGGAGTC ATTCCCTGCA GCCACTAGGG GGCAGCCGCC
17151 ACCGCTCAG CAGCCCTGGG AGGCGGCACG GCAGGTGCG CCTTGGGAGG
17201 GCTGAGGCAA AGACCCGGG TAGAAAGGCG GCCCCAGCT CTGCGAGACC
17251 CCTGCCCTCT TGTCCAGTCC CTTCCGAGGG TCCGCAGGTG AGAGCAGCCT
17301 GCCCTGCATC CCAGGCTCTG GTTCCAGGGT CCAGGGCCCT GCGCTGCCAC
17351 CTCCCTCGTG CTTCAGCCAA GAAAATGGGG GTGCAAGTAG GGTGTTTGGG
17401 GTCCCAGAGA CGCAGGCGCC GCGGCGCGAT CTTCCTGGGC AGGAGGGCAG
17451 GGCTCCCCAA CCTGCCTGAG CCGGGGTGGG GGTCCAGGTC CCCCACTTGC
17501 CCTTGTGGGA AAATCCCTGT CTCAGCAGAA TGGGCCAAGG TCACGCAGGT
17551 CTCCCCAGCA CGTGTTAATT TGGTTAATAA AACTGTGGAT CAAGGAGGCC
17601 AGTAGGCACT AACTGGGGAT GACAGGGTGG CAGCCCTGTC TGGGAAGTGC
17651 AGGGACTCCC CACCTCCTGT GGCCTGTCGA GACCCAAGCT GGGGACAGAG
17701 CTGCCACCTG CCTCCTGCAT GGTGGGCGCC AGGCCACCAT AGCCTGGGGG
17751 AGGGGGCTTT TGCCCAGAGA GCACGCCTCT CCCCACCGCA GACCCCTGGG
17801 GTGCGCCCAA CCCGTCCCAC CCTGCCCAC ACATGCCTCT CCCCTGGCTG
17851 CCACCAAGCC TGGGCCTGTG CTCCTGGCCC TGCCCTCTGC CCCAGGCCAT
17901 CTCCTCCCCT GCTGCCCCCC CCCCGCCGT CGTGTCCCTC TGCCACAGAG
17951 GGGGGGCCTC ACAGCTGAAG CCACACGTGG CTGGGACCTG GCTCCCGTCA
18001 CCGCCTCCGT CCTGTGAAGT GGAGGAAGCC TGGTGCACAG GGGTGCTGTG
18051 GCGATGTGGG GGGCCCTGAG GTCCTGCTGC CAGCCAGGGG GAGGGGGGCG
18101 GAGGTCCTGG GATCTGGGGT CCAGAGTTCT AGTCAAGGCA GGGCTGGGCA
18151 GGAGGGGGT CCCCCTCCCC ACCTTCCACT TGGGGCTGCT CTCCAGAAGA
18201 GAAAGCGGAT GCCTACCAGC CCAGCCCCTC AGACTTGGAC CATGCCCCTC
18251 CGGCATCTGT GGGAGTCCTG CCAGACAGCC CCTGGGCTGC GGGAAGGGAC
18301 CGCGCCCCAT CCCATCCTCA TCCCTGCAGT AGCTGGTGGC TGCCTGCCCG
18351 GCGCAGGGGC CTGCTGAACA GGGGACTGCC CTGTCCAGCC CACCCACGGG
18401 ACTCAAGTC CACACAGGCA GCAGAGTCGG CAGCGGTGGG CAGAGTGGGG
18451 GGGCATCACC ATGGCTCCTC AGGGACTGGT CAAGGGTGTG ATGCCTGGCC
18501 TGGCAGGACC TGCAGTTTCA CCCCCGGGGC CAGCTGTGGC CTGTGCCCCG
18551 CCAGAGGGCA GTGCAGCCCC TGGGGCCAGC ACACAGGAGG CGGCAGCTCA
```

FIGURE 3F

```
18601 GGGTCCTGTC CCATCTGCCC AGGCTAGGGA GCAAAGCAGG ATCAGGGCGA
18651 GGCTGCGAGG CTGGGGGAAG GCAGGGCTGG CCGCTGGGGA GCGCTCGGTC
18701 CGCAGGCTGT GCGGTGAGAG CCACTGGGTG AGGCTTCCCG GGGGGCACAG
18751 CTGCCCCGAG GGGCCGGCTC AAGGCTGTCC CTGCAGCAGC ACGTGTTGGT
18801 GCTTGCCTGC CCCCCCCGCA GCGCCACACC GCGGCCTCTG TGGAGCCCGT
18851 TCTCTTCCCT TGAAGTCCTG CTTGCGCACT CCTGGGCGTT TCTGGCTAGC
18901 ACCTTTTTGG CTTTTAGGGA CGGGTTAGTG TCCCTTCCTC AGATGGCCCG
18951 GCCTGGACAC ACCCCATGCA TGGGCCTTAG CCCCCACTTT CTGGGCCAGC
19001 CTTATCACTT TGGGCACTGT GTCAC (SEQ ID NO:3)
```

FEATURES:

Start:    3000
Exon:     3000-3059
Intron:   3060-7495
Exon:     7496-7654
Intron:   7655-8913
Exon:     8914-9029
Intron:   9030-9885
Exon:     9886-10014
Intron:   10015-10755
Exon:     10756-10831
Intron:   10832-11644
Exon:     11645-11722
Intron:   11723-12071
Exon:     12072-12196
Intron:   12197-12287
Exon:     12288-12454
Intron:   12455-12690
Exon:     12691-12884
Intron:   12885-13204
Exon:     13205-13361
Intron:   13362-13437
Exon:     13438-13551
Intron:   13552-13964
Exon:     13965-14159
Intron:   14160-14643
Exon:     14644-14720
Intron:   14721-14947
Exon:     14948-15094
Intron:   15095-15182
Exon:     15183-15344
Intron:   15345-15811
Exon:     15812-16024
Stop:     16025

CHROMOSOME MAP POSITION:
Chromosome 8

FIGURE 3G

SEQUENCE LISTING

<160> NUMBER OF SEQ ID NOS: 4

<210> SEQ ID NO 1
<211> LENGTH: 2469
<212> TYPE: DNA

-continued

<213> ORGANISM: Human

<400> SEQUENCE: 1

```
tcgcggccca ggtggtgcgg gcggccctag cccggctgcg gagcgctgcg cgagcggcgg      60
gctggctgac cccgagggac ccccagcgca gcgggtgcgg cgatgatcct ggaggagagg     120
ccggacggcg cgggcgccgg cgaggagagc ccgcggctgc agatatctag gagaaaaccc     180
aggaaaacac gtgtgagctc tttacgggga agacgggaag gcctgagaga cgtgtgtgcg     240
tggagagggt gtcgggtcca cagaggggaa gacccagtgc gtgtgcacgt tggccccatg     300
aatccgcagc ttcatgcagt gggctgtgac tccctgacgc agatccagtg cggccagctg     360
cagagccgca gggcccagat tcaccagcag attgacaagg agctgcagat gcggacgggc     420
gctgagaacc tctacagagc caccagcaac aaccgggtga gagagacggt cgccctggag     480
ctgagctacg tcaactccaa cctgcagctg ctgaaggagg agctggagga gctcagcggt     540
ggcgtggacc ctggccggca tgggagcgaa gctgtcactg tccccatgat ccccctgggc     600
ctgaaggaga ccaaggagct ggactggtct acaccgctga aggagctgat ctcagtgcac     660
tttggagagg acggcgcctc ctacgaggca gaaatcaggg agctggaggc cctgcggcag     720
gccatgcgga cccccagccg gaatgagtcg ggcctggagc tgctcacagc ctattacaac     780
cagctgtgct tcctggatgc gcgcttcctc accccctgcca ggagcctcgg gctcttcttc     840
cactggtacg actcgcttac tggggtcccg gcccagcagc gtgccctggc cttcgagaag     900
ggcagcgttc tcttcaacat cggtgccctc cacacgcaga ttggggcgcg ccaggaccgc     960
tcctgcaccg aggtgcccg ccgcgctatg gaggccttcc agaggggccgc tggggccttc    1020
agcctcctga gggagaactt ctcccatgcg ccgagcccag acatgagcgc tgcgtccctc    1080
tgcgcactgg agcagctcat gatggcccag gcccaggaat gtgtgtttga gggcctctca    1140
ccacctgcct ccatggcccc ccaagactgc ctggcccagc tgcgcctggc gcaggaggcc    1200
gcccaggtgg cagccgagta caggctagtg caccggacca tggcccagcc acccgtccac    1260
gactacgtgc ctgtctcctg gactgccctg gtgcatgtca aggccgagta cttccgctcc    1320
ctggcccact accacgtagc catggccctc tgcgacggct ccccagcgac cgagggagag    1380
ctccccacgc acgagcaggt cttcctgcag ccccccacct cctctaagcc ccgaggccct    1440
gtgctgccgc aggagctgga ggagcgcagg cagcttggca aggcacacct gaagcgtgcc    1500
atcctggggc aggaggaggc gctgcggctg cacgccctgt gccgcgtcct gcgcgaggtg    1560
gacctgcttc gggctgtgat ctcccagacg ctgcagcgct cactggccaa gtatgcggag    1620
ctcgaccgtg aggatgactt ctgtgaggct gccgaggccc cggacatcca gcctaagacc    1680
caccagaagc cagaggccag gatgccacgc ctgtcccagg ggaagggggcc tgacatcttc    1740
catcggctgg ggcccctgtc tgtgttctca gccaagaacc ggtggcggct ggtggggccc    1800
gtccacctga cccgaggaga gggcggcttt ggcctcacgc ttcggggaga ctcgcctgtc    1860
ctcatcgctg ccgtcattcc agggagccag gccgcggcgg ctggcctgaa ggagggcgac    1920
tacattgtgt cagtgaatgg gcagccatgc aggtggtgga gacacgcgga ggtggtgacg    1980
gagctgaagg ctgcgggaga ggcgggcgcc agcctgcagg tggtcgcgct gctgcccagc    2040
tctagactgc ccagcttggg ggaccgccgg cccgtcctgc tgggccccag ggggcttcta    2100
aggagccaga gggagcatgg ttgcaagacc ccggcatcca cgtgggccag tcccggcccc    2160
ctcctcaact ggagccgaaa ggcccagcag ggcaagactg gaggctgccc ccagccctgt    2220
gccccagtga agccagctcc gccctcatcc ttgaagcacc caggggtggcc gtgagggcca    2280
```

```
ggatccctgc acgccctcag ccctggctcc agctggcagc aagcaccgag catgccctcc    2340
ccacccagag gacctccggg caatgcctgt cccgcctcat gctggaggct gcctcgggca    2400
cctgcctgcc cattaaagac tggtcagacc tgtctgaaaa aaaaaaaaa aaaaaaaaa     2460 aaaaaaaaa                                                            2469
```

<210> SEQ ID NO 2
<211> LENGTH: 723
<212> TYPE: PRT
<213> ORGANISM: Human

<400> SEQUENCE: 2

```
Met Ile Leu Glu Glu Arg Pro Asp Gly Ala Gly Ala Gly Glu Ser
 1               5                  10                  15

Pro Arg Leu Gln Ile Ser Arg Arg Lys Pro Arg Lys Thr Arg Val Ser
                20                  25                  30

Ser Leu Arg Gly Arg Arg Glu Gly Leu Arg Asp Val Cys Ala Trp Arg
            35                  40                  45

Gly Cys Arg Val His Arg Gly Glu Asp Pro Val Arg Val His Val Gly
        50                  55                  60

Pro Met Asn Pro Gln Leu His Ala Val Gly Cys Asp Ser Leu Thr Gln
65                  70                  75                  80

Ile Gln Cys Gly Gln Leu Gln Ser Arg Arg Ala Gln Ile His Gln Gln
                85                  90                  95

Ile Asp Lys Glu Leu Gln Met Arg Thr Gly Ala Glu Asn Leu Tyr Arg
            100                 105                 110

Ala Thr Ser Asn Asn Arg Val Arg Glu Thr Val Ala Leu Glu Leu Ser
        115                 120                 125

Tyr Val Asn Ser Asn Leu Gln Leu Leu Lys Glu Glu Leu Glu Glu Leu
    130                 135                 140

Ser Gly Gly Val Asp Pro Gly Arg His Gly Ser Glu Ala Val Thr Val
145                 150                 155                 160

Pro Met Ile Pro Leu Gly Leu Lys Glu Thr Lys Glu Leu Asp Trp Ser
                165                 170                 175

Thr Pro Leu Lys Glu Leu Ile Ser Val His Phe Gly Asp Gly Ala
            180                 185                 190

Ser Tyr Glu Ala Glu Ile Arg Glu Leu Glu Ala Leu Arg Gln Ala Met
        195                 200                 205

Arg Thr Pro Ser Arg Asn Glu Ser Gly Leu Glu Leu Leu Thr Ala Tyr
    210                 215                 220

Tyr Asn Gln Leu Cys Phe Leu Asp Ala Arg Phe Leu Thr Pro Ala Arg
225                 230                 235                 240

Ser Leu Gly Leu Phe Phe His Trp Tyr Asp Ser Leu Thr Gly Val Pro
                245                 250                 255

Ala Gln Gln Arg Ala Leu Ala Phe Glu Lys Gly Ser Val Leu Phe Asn
            260                 265                 270

Ile Gly Ala Leu His Thr Gln Ile Gly Ala Arg Gln Asp Arg Ser Cys
        275                 280                 285

Thr Glu Gly Ala Arg Arg Ala Met Glu Ala Phe Gln Arg Ala Ala Gly
    290                 295                 300

Ala Phe Ser Leu Leu Arg Glu Asn Phe Ser His Ala Pro Ser Pro Asp
305                 310                 315                 320

Met Ser Ala Ala Ser Leu Cys Ala Leu Glu Gln Leu Met Met Ala Gln
                325                 330                 335
```

-continued

```
Ala Gln Glu Cys Val Phe Glu Gly Leu Ser Pro Ala Ser Met Ala
            340                 345                 350

Pro Gln Asp Cys Leu Ala Gln Leu Arg Leu Ala Gln Glu Ala Gln
            355                 360                 365

Val Ala Ala Glu Tyr Arg Leu Val His Arg Thr Met Ala Gln Pro Pro
            370                 375                 380

Val His Asp Tyr Val Pro Val Ser Trp Thr Ala Leu Val His Val Lys
385                 390                 395                 400

Ala Glu Tyr Phe Arg Ser Leu Ala His Tyr His Val Ala Met Ala Leu
                    405                 410                 415

Cys Asp Gly Ser Pro Ala Thr Glu Gly Glu Leu Pro Thr His Glu Gln
            420                 425                 430

Val Phe Leu Gln Pro Pro Thr Ser Ser Lys Pro Arg Gly Pro Val Leu
            435                 440                 445

Pro Gln Glu Leu Glu Glu Arg Arg Gln Leu Gly Lys Ala His Leu Lys
    450                 455                 460

Arg Ala Ile Leu Gly Gln Glu Glu Ala Leu Arg Leu His Ala Leu Cys
465                 470                 475                 480

Arg Val Leu Arg Glu Val Asp Leu Leu Arg Ala Val Ile Ser Gln Thr
                485                 490                 495

Leu Gln Arg Ser Leu Ala Lys Tyr Ala Glu Leu Asp Arg Glu Asp Asp
            500                 505                 510

Phe Cys Glu Ala Ala Glu Ala Pro Asp Ile Gln Pro Lys Thr His Gln
            515                 520                 525

Lys Pro Glu Ala Arg Met Pro Arg Leu Ser Gln Gly Lys Gly Pro Asp
    530                 535                 540

Ile Phe His Arg Leu Gly Pro Leu Ser Val Phe Ser Ala Lys Asn Arg
545                 550                 555                 560

Trp Arg Leu Val Gly Pro Val His Leu Thr Arg Gly Glu Gly Gly Phe
                565                 570                 575

Gly Leu Thr Leu Arg Gly Asp Ser Pro Val Leu Ile Ala Ala Val Ile
            580                 585                 590

Pro Gly Ser Gln Ala Ala Ala Gly Leu Lys Glu Gly Asp Tyr Ile
    595                 600                 605

Val Ser Val Asn Gly Gln Pro Cys Arg Trp Trp Arg His Ala Glu Val
610                 615                 620

Val Thr Glu Leu Lys Ala Ala Gly Glu Ala Gly Ala Ser Leu Gln Val
625                 630                 635                 640

Val Ser Leu Leu Pro Ser Ser Arg Leu Pro Ser Leu Gly Asp Arg Arg
                645                 650                 655

Pro Val Leu Leu Gly Pro Arg Gly Leu Leu Arg Ser Gln Arg Glu His
            660                 665                 670

Gly Cys Lys Thr Pro Ala Ser Thr Trp Ala Ser Pro Arg Pro Leu Leu
            675                 680                 685

Asn Trp Ser Arg Lys Ala Gln Gln Gly Lys Thr Gly Gly Cys Pro Gln
    690                 695                 700

Pro Cys Ala Pro Val Lys Pro Ala Pro Pro Ser Ser Leu Lys His Pro
705                 710                 715                 720

Gly Trp Pro

<210> SEQ ID NO 3
<211> LENGTH: 19025
<212> TYPE: DNA
```

<213> ORGANISM: Human

<400> SEQUENCE: 3

| | | | | | |
|---|---|---|---|---|---|
| ccaccctgtc | tcaaaaaaaa | aaaaaaaggc | cagtcacagt | ggctcacacc | tataatccca | 60 |
| acactttggg | aggccaaggc | aggcagatca | ctggagctca | gaagttcaag | accagcctgg | 120 |
| gcaacagggc | gaaaccctgt | ctcaattttt | ttttccttta | taattacaa | agagaaaac | 180 |
| gagcataaag | cagccccatc | agcaattatc | acctcatctg | caaaaggtcc | cggcgctcac | 240 |
| tgccgtgccc | ctcccgccgc | tgtccagttc | cctgcctgtc | acaccaaaat | tctcctctac | 300 |
| tttctcacct | cccatccttt | cattttccc | cctaaatttt | taaacttcag | aagtgcacaa | 360 |
| tacacatgta | acaaacccac | acatgtacct | ccaaatctaa | ataatttaa | aaaacaaaa | 420 |
| aggaaactct | aaatttttg | agtgcagtga | tacattcttg | ctgtgccaaa | tccagtaaca | 480 |
| cagaagcatg | caaagaaaaa | ggcagcacca | ccccctcca | acacacacac | acacacacac | 540 |
| acacgcacac | acgcacatat | gcacgcacac | acacgcacac | gcacacacgc | acacgcacac | 600 |
| actccagcct | gggcgacaag | agcaagactc | catctcaata | aataaataaa | gaaaatagta | 660 |
| attgaatatt | ttccttcagg | aaacagcacc | ctgcaggag | gggaagtctt | atgaccctca | 720 |
| aagtttgaga | gcctctctta | acttcccaat | ggcctctgtc | tgctgaacca | agaagcctgc | 780 |
| aaaacaaata | cgtaagaact | ggataccatt | tcagtcacac | atgcttgctg | acagtcactg | 840 |
| atatggtaat | gcctcctgta | cacatagctg | actctgaaga | ctgctaagag | ggtttgggtc | 900 |
| tctgctgtac | aggaccttgg | cagcctgcaa | ggagatgact | cacatggaag | tccccacaca | 960 |
| agtgcaccca | gtgtgaactt | tggaagcatc | ggcccatgct | caggcccaca | ggtaagatgg | 1020 |
| ccaggagccc | ctgcccttga | ggaaacttga | accacagagc | tgctggcgaa | gggggtgggt | 1080 |
| gaaggtctca | tgtagcctgt | gtgattcagg | cagaagtgag | aaggacgggt | gggaacccac | 1140 |
| caagtggacg | acaagctgaa | gggctcccag | ggagcagaca | cttcaagggc | cccaaaaggc | 1200 |
| caggagaaag | aaaaaaaaaa | gccgggtatg | gtggctcatc | cctgtaatcc | agcacttttg | 1260 |
| ggaggttgag | gcagatgaat | tgcttgagcc | cagaagtttg | agaccagcct | gggcctgggc | 1320 |
| aatgtggcga | aaccctgtct | ctacaaaata | tacaaaaatt | agccgggtgt | ggtggtgcaa | 1380 |
| gcctgtagtc | ccagctattc | aggaggctga | ggtgggagga | tcacatgagc | ccaggaggtg | 1440 |
| gaggctgcag | tgagctgtga | tcgtaccact | gcactccggc | ctggggaaca | gagtgaggcc | 1500 |
| ctgtctcaaa | aggccaggag | tggaagacag | gccctagcca | ggaggtttca | cgtggctggc | 1560 |
| agggccctta | tgagaaggct | gttgctggga | ggggcctgct | gcagatggct | gcggcagacc | 1620 |
| acggagctta | gccttcagga | tttagatctg | gggatgacag | gctcctgtgt | gcttgttgcg | 1680 |
| gagccgggag | cacaggcacc | agaatgatcc | cagggctcag | ctccaaggct | ccgctgggcc | 1740 |
| tgtggtgggg | cagtgaacgt | ggacaagacc | tgggcttcag | aggaacttga | tgaccaggag | 1800 |
| ccgtggttac | cgcctgtgcc | ctggccttcc | tgctcttcaa | agggtgtgtt | ctgagctgag | 1860 |
| gcgagaccca | cacgaaatcc | gagcgggctc | cggagtcacc | agacacctag | ggaagtatgg | 1920 |
| aaggcccgga | aggacacaca | cagccgggtg | agccccgcag | ggagctgtgc | agtctcaggt | 1980 |
| cgtccagtcc | tggggctgca | ggccagttct | ccaagcaggt | ggtcctggag | gcaagctggt | 2040 |
| tttgaaagta | ggttctgaaa | ataggtcagt | ccaggaaaca | agctctggaa | gtaaagagat | 2100 |
| tcggaaagca | ggttcgttct | ggaaacaagt | tctacaaaca | ggtagttctg | aaagcacgtg | 2160 |
| ggttccagag | gcaggtgcta | gaaggatgtg | ggttctgtac | ggaggttctg | gagggaggcg | 2220 |
| ggttctggac | ggaggttctg | gaaggaggcg | ggttctggag | gccggttttg | gaagcaggac | 2280 |

-continued

```
gacaccgaca gaggcgcctc ggactggggc caggcctgga gcctccgctc cgcgggcaga    2340
gagaagaaag caggcattgt cggaggactc acacaagcac ttgtccctaa caaaaccgtt    2400
tttaaaaacc ccattgtgaa cattttggga acaagcctct tagagggtcc cgttgccggg    2460
gtgacaggac gaaacggcgc gagcgggcag actcctggag tccccgcaaa gggagccgag    2520
gagctaggcg cgccgagtcc aggtccgccc tgactctcag cttgggacgt tccgtatagt    2580
ttttttctcc gtttcccgaa cttctcccgc acgctcagcg gccgccgcgg cgcatgcgca    2640
gtacaacctg ccagccagcc gcgggcgttc cggccgcgt tgccagggt taccgtcccg     2700 cgggcgggcg gagctggccg tccagagccc gccttcctgg aactctggtt ggctgatata    2760
gctgtccgtc gaagcggcat gccgcctat tgggcaatgg ccagcttcgc acgccagacc     2820
cgtgccccgc ccagccgcgc gcgggccgc ccccactcag gagggacagt cggggaccgg      2880
cgcgggcact caggagcccg cggcccaggt ggtgcgggcg ccctagccc ggctgcggag      2940 cgctgcgcga gcggcgggct ggctgacccc gagggacccc cagcgcagcg ggtgcggcga    3000
tgatcctgga ggagaggccg gacggcgcgg gcgccggcga ggagagcccg cggctgcagg    3060
tgcgcagaac tggcgcggcg gcgggaggag gggcccggaa tcccggcctt ttcctgcccc    3120
ccctcgaggc gcgttccggg cgcccccctc ctacgtactc attcggcccg gacgcaggca    3180
gggaaactga ggccagagcc tgcgtgccct cctcctctga gctcggtgga ggtgcttcca    3240
ggccactcat gtgagccggg aaatgcggac agccaaagtc tggatcatcc tcaccgctga    3300
agcgggttgg ggggacgccc tcctcgtgtc ccccttctgg gcggatgtgg ggctgggatc    3360
tgtgagcgcc ctccccacac ccgccatcgt gttccttttcc ggcacctgta cagcctcctt    3420
ccctagttcg gtcctccctc tgcatccgct caggaactgc atgcccattg ggtgcactgg    3480
tagcagcggg cagcgaagcc tcctgggtat gggaaaccga gagaggtctt cccggctggc    3540
ctcttctcac ttcccaaacc tccttcccctt ctgaagtccc taacccgggg tgctgactgg    3600
gcaagtggga ggggtgggca gggctgtgga gacctgctga gtctgtgcct gggaaggagg    3660
ggacgtctgt gggccttgct ctgcagccca gagcctgctt gttccctgcg gaccagctcg    3720
aggctgcccc agtcctcctg ccaggccctg ggcgcccacg cccgccacgg gctttcagcc    3780
gcgggctgct cctgctcctc gccccgggtg agcctttgat agccgcgggc cctcctcccc    3840
tctgggacgt cagactgtgt tgtccctggg ctggttctac tcggctttgg tgtttgggt      3900 taggtctcct agaggaggag gcggtgctat cagccagggt ttggcttcag gtcactgggc    3960
tggtgatgct gaccgtagcc ctcaaggtcg cccttcttgc ccaccccgag gcgtgccaga    4020
ggctgcagca cctcctgggc actggaggga aagaggcagc ctgtgcctgc ccctgtgaa    4080 cttgctctgt cagggcggcc atgcctgcag gtggcctggg acggcacatg ttgttttggg    4140
tggaatgttt gggaggctgt acaaacaaga tgtcccagag ggctccggag gtgacgcttt    4200
tcaggctggg ggctgtgcct gggctccctg tcctggccct ccctgggctg ccaccttgga    4260
aagttgggga gaagctgttt ccaggctgcc gtgtctctca cagcgtccag aaatgacccc    4320
acagtcaggg tactggggag gggcccgtgg gaggtggcag tggggcggag gcaggccctg    4380
tgtcacacgc gcaccactca ggctgtcctg ccatctggaa agtcttcccc gatgcctgct    4440
gccgggctag agtgaggcct gttccacccc catcaggctg gcccccaaac tggccctaaa    4500
gctcagagtt cagtgggtca gggtcggtc gttcatccac ttagaggcca cacctgggcc     4560
tgaggccctg tggacaggtc tgggtgactt gtatttgccc caggcgtgat gagagcaggc    4620
```

-continued

| | | | | |
|---|---|---|---|---|
| ttccagcaag | cgcttacctg | gtgccagggc | cagtgctaca | gctggagtcc | tgccattggt | 4680 |
| gcctcccaag | ccctgggcct | cagcccgtct | gatgaacagg | gtgagtaagt | ggccaaggct | 4740 |
| gccaagctgg | gaaggggaga | agcctggcac | ggcccaggt | ggccaaccca | gctgccgtcc | 4800 |
| ctcccgcagg | ggctgcaggg | gctcccgggg | gaggaccaca | aggaatacag | cctggctgta | 4860 |
| tgcagaaggt | tctgtggttt | cctggggagg | ccagtgggag | aagggggagc | aggctgcaga | 4920 |
| gggagagcgt | tggagcagca | ggtgggcagg | gtggctgtgc | cccctcacc | tggtctccag | 4980 |
| catgccgagt | gggtcagcct | gaggttcccc | agcctggctg | gacaggagca | ccctctgggt | 5040 |
| gctggttaca | ggttcccagg | cccctgccca | ggtagattgg | gctccaggaa | gagggtgct | 5100 |
| caggaagcac | cagtgcctgg | gtaccccagg | gagcatcaga | gagagtggga | gtccctgccg | 5160 |
| tgagtggcca | gtctatgatt | cctctggcgt | gcgtgctgct | tatagccctg | tgtcccagga | 5220 |
| gacacctgtg | cagcaatgcc | ctttgaattc | tgttccctca | tcagtggggg | gcagagatgg | 5280 |
| tgggtcaggt | gggtgctggg | cttccaccct | cctgggcctt | ccagttcttg | cattcaggtg | 5340 |
| agacttcagt | gggggcagag | gagagggta | cctgagatgg | gtggctgtca | gcatacaggg | 5400 |
| tgcccagggc | cagggctctg | aagggaaaaa | gctggtttgc | tccaggtggg | tgacctctcc | 5460 |
| ctggggactg | cctggcccag | ggccagggga | tcctggggga | gagtggaggt | ctggccctgc | 5520 |
| tctgatgttt | tgctgttccc | agacctgggc | tgggataact | atctctgcct | tttgcccgtc | 5580 |
| cccaggtcag | ccccactctg | gccagggcca | cactgtttcc | tcctgggcag | aggagcccca | 5640 |
| gtgtcagggt | tgggggctg | tttctctgtt | cttcgtccct | ctccatcgag | gcatggccag | 5700 |
| gcccttcatg | tgtggctgcc | ctcgggacc | cccacagacc | acagcctctc | tgtcctttcc | 5760 |
| taatgcaagg | cggaaatggc | cacagtgggg | tgtcagggca | ccgtggacgt | ggggtgggg | 5820 |
| agctccaggt | cacctttgtc | tccagagggt | ggggaggttg | tagcaggagt | aggggcctga | 5880 |
| acgcctgtgt | ctatgcccct | tccactgggc | tcaaccttca | acccagtgtg | aaagtgggg | 5940 |
| catgggccgc | ccacctccaa | ggtctaccca | gcctcaaagg | tccggctcgg | gtctgctcct | 6000 |
| ccgcctgtag | gccgggaagt | cacttggcct | gcagggagca | ctgcgggtag | ggaggccgag | 6060 |
| gaatggacca | ggcccacagc | aggtgcctgt | ggggctccaa | ggggccaggc | tccccgcagc | 6120 |
| tctcctgggg | ccaggagggg | agcagggacc | tggctgggtg | tctgatgccc | gtcgcacagc | 6180 |
| cagagccctt | aaagctgctg | gagccttgca | gcggggcctt | tgcggggagg | gggtgtagct | 6240 |
| gcggtgggtg | gcacggggt | ctcctaggta | ctgggcagag | gccctcgagg | tggtagcgcc | 6300 |
| ggtgggaaag | gtagggatgg | gaggcggggg | tgggcgggcc | tcaggttcag | ggagcttctc | 6360 |
| agatctgagg | cgcccatgcc | cctctcccac | ctgtgggcct | ctccagcccg | agtccctgaa | 6420 |
| gcagctctgg | aggtaatttc | ttttctggag | gaggcggag | tgagaaacgg | gagcagggtg | 6480 |
| agggttccca | agtgcacatc | ggcccgtccg | ctgctgggtg | gtgtccacgg | gggcagggct | 6540 |
| gggctggggg | aggccagggt | cctgggccgg | cacaccctcc | ttccggctgc | ctgtgtccct | 6600 |
| ccctccagct | gcctgtgtcc | atccctccgg | ccgcctgtgt | ccctccctcc | ggcccctaag | 6660 |
| cgccaactca | tcttcagttc | agggacctcc | gtcaggctcc | ctcaccccag | cactcagcag | 6720 |
| gaggctgccg | gcctgggtgt | ccaggggatg | gtgcgggtgt | ccagcagaca | gtacaggggt | 6780 |
| ttgggggatg | gtacaggtgt | ctgggggatg | gcgtgggtgt | ccagcagatg | gcgcagggt | 6840 |
| ttgggggatg | gcacaggtgt | ctggggaca | atgcggggt | ttgggggatg | gcgtgggttc | 6900 |
| cagggatgg | tgcaggggct | tggggatgg | tgtgggttcc | agggaccgt | gtgggggttt | 6960 |
| gggatggcg | tgggtccag | ggatggtgc | aggggcttgg | gggatggtgt | gggttccagg | 7020 |

-continued

```
ggacggtgcg ggggcttggg gatggcgtgg gttccagggg acggtgtggg ggtttgggga    7080
tggcgtgggt tccagggac ggtgcctcat cctccagtct ctgtctctgc cttcccatgg     7140
ccacctccat gtgactgtgt tcaaattccc cacctcgtat aaggacccct gtcactgcga    7200
ttaaggaccc cctactccag ggtggcctca tcttaactca ttatatctgc aaagacccta    7260
tttctagaaa aattgcagtc acaggtactg ggagtcagga cttgaacctg tcttttgtgg    7320
ggacacaatt cacccataat agatggtcac ccgctcagct ggctgctgtg attttggggg    7380
gctggacgag caggccttct gtctaggaaa tcaaaccttt cttgtataat gggaataaac    7440
taattaaaat gcacacaaag atctcgttca cattagcaaa aagaactctc tccagatatc    7500
taggagaaaa cccaggaaaa cacgtgtgag ctctttacgg ggaagacggg aaggcctgag    7560
agacgtgtgt gcgtggagag ggtgtcgggt ccacagaggg gaagacccag tgcgtgtgca    7620
cgttggcccc atgaatccgc agcttcatgc agtggtaggt cagtttcatg gtggcaagat    7680
tcaccttcag acgccacaag gtcctgggga agaagaggtc ctgtctcccg acaagggcgg    7740
gaagcagtcc caggagccac cagaggcctt gtcttgctgc tgactggcag aaatggccag    7800
gttggccacg cctgactcag accaggctcg ccccagggct gggtgggagt cagtgtccct    7860
gagcagtgag ccctgagcag cactgtgggt ctcaaagcat ggaaggagtg ggtgctggag    7920
aggcaagcca gccagcccac gcctgggagc ccacccaggg gacagccaca ggtagctgca    7980
aataatcttg tccgggtgga gacccaggca ttcccacatg gccacgggga agagtggggg    8040
ttgggaggcc atggtgagag ggagggacac gtgaggatca tgtgggcagg accccaacac    8100
cacaagggtg gggtgggctg aggcatgaaa ctggatctcc ctagagtgaa atgtaagctc    8160
cagcacgctg gcaccactga cgacacagga gccatcaaag tccagaaggg gccccgctgg    8220
gcacgcccca ctctttcgcc atggctggtg ctgggcaggg ccgcggggct gcagtctggg    8280
tgcaaggctc agagtcattt ctctgtggat agggagggca cgggtgtgcg ttcgcttcga    8340
gaaccattcc caaagtcaga ccgcagcctc tgcaccaacc atcgggggcc agtgccgcc    8400 cccagagcct cagggaccct gtcctttgag cccacgccta aacccacatg ggaatgattt    8460
ggaggcgtgg gtgagttgga tgggaaaaaa attgggaggg gcaaggggg gatccagaat    8520 gaaatccaga agcgcagaag gaaggctgtg aggagcagtg ggccgcctcc tgcagggctc    8580
ccggagcccc tacttgtcca ggctgcctgg tgagaccctg gcttctggtg tccttggcag    8640
gtgccagcct cccccgctga cccccatcac gagtcagcag cttaccccac cgaccacgtc    8700
cttctgcatt gactgcctcc tgtcctgctc tggccaggcc tgtgttcaca ctagttctgt    8760
ccagcccctc cctgtgaggc cagctccagc cccagcgcat ggtgaccatc ccgttaccca    8820
tgggcaggat gcactcctct cagtggctgg cgaggcgcag cctggtgcgg gcgccacggg    8880
gtcgggctgt gatcgcctgt ggcctccctg cagggctgtg actccctgac gcagatccag    8940
tgcggccagc tgcagagccg cagggcccag attcaccagc agattgacaa ggagctgcag    9000
atgcggacgg gcgctgagaa cctctacagg tcagtgcttg agactgcccg gccccgggag    9060
cagggcccac ctggtgagg ggggcaggac agccacgcag gcagatgtct gccccatggc    9120
cgggtcacag agacaggtgc atgagcagct gggtcctggt gggcacgtag tacacgtgat    9180
gctcagccat gaccctcaca gacctgcctc cgtgggcctc tgtgctgggc tggaggtgcc    9240
aggaaaccag tgtccctgcc gggtgtgcag cttgggaagc cccaacagtg cacgtggggg    9300
cttctcagaa gaggcatggt tgaggctgag ctgtggcagg tgacggcgcg tcccaaggtt    9360
```

-continued

| | | | | |
|---|---|---|---|---|
| ggggacctgg | gaggggtgg | aagacctggg | ctgcctcttc | cttagagcac accgcctgtg | 9420 |
| tgccacacat | gtgcgtgtga | gtgcccctcg | gtccccttag | cacctgctac ctcgctgccc | 9480 |
| ccatcctggc | cttccctggg | gacctccggt | cccttttgcca | ggccctgatg caggcacaga | 9540 |
| gaggtgtgtg | gctctcaccc | accatccaag | gagtgatgtt | tgagtgctgt cgagggctgt | 9600 |
| atgagcccca | aagaaagccg | tggtgctgag | ggaggtgccc | ccaggccaga gtcggaacat | 9660 |
| gcaggtgctg | gggtcggggt | gatgaactgt | aggggggcatc | acctgtgagc ccccggatcc | 9720 |
| cactgctgcc | cctgccccac | ccatgggggg | cagaccctgt | cagcgacgtc ctctgcaggg | 9780 |
| tgggcttgga | gctttgacag | gtcagctggc | aggacggctg | cagtgggcac ggggcctttg | 9840 |
| gctctgcctt | ggggctgggc | tttcaactgc | cgcggcctcc | ctcagagcca ccagcaacaa | 9900 |
| ccgggtgaga | gagacggtcg | ccctggagct | gagctacgtc | aactccaacc tgcagctgct | 9960 |
| gaaggaggag | ctggaggagc | tcagcggtgg | cgtggaccct | ggccggcatg ggaggtgcgg | 10020 |
| gtgggggccg | ggacagcacg | tgcgtgtatg | tgtgtgcacg | tgtgcgtgtg tgtgtgcatg | 10080 |
| tgtgtgcacg | catgtgtgtc | tctgtgtgta | tatgtgtgca | ttgtctgtgt gtgtgcgtgt | 10140 |
| gtgcatgtgt | gtgcatgcat | gtctgtgcgc | gtgtgtctgt | gtgcatgtgt ctgtgcatct | 10200 |
| ctgtgtgtgt | gcgtgtgtct | ctgtgtgtat | atgtgtgcat | tgtgtgtgtg catgtgtgtg | 10260 |
| tgcatgcgtc | tgtgtgcgcg | tgtgtctgtg | tgtctgcatg | tgtctgtgtg tgcatctctg | 10320 |
| tgcgtgtgtc | tgtgtgcacg | tgtctgcgtg | cgtgtgcatg | tctgcgtgta tgtgggtgtg | 10380 |
| tgtttgcctc | tatgtgtgcg | tgtatgcacg | tgtgtctgtg | tgtgtctgtg tgtgcgtgtg | 10440 |
| tgtgtgtgtc | tgcacgtgtg | tgcatatatg | tgtgtgcgtg | cgcatgtgtg tctgcatgtg | 10500 |
| tatgcacgca | tgtgtttgtg | tgtgtgtgtg | cgcgtgcatg | tgtgtgtctc tgtgtgtgtg | 10560 |
| tgtttgctttt | tggggcggtt | taggacggtg | gggggtggtg | cacaggtgca aggatgcccc | 10620 |
| ccaggacaca | ggcgcacgtg | cacacccatg | agggagggag | gcaccctgtg ccacagagcc | 10680 |
| ctaggagtgg | accccgggct | gccgtgggca | gcagggtttg | gccttacagt ctgaagtcga | 10740 |
| tgcttctggt | tacagcgaag | ctgtcactgt | ccccatgatc | cccctgggcc tgaaggagac | 10800 |
| caaggagctg | gactggtcta | caccgctgaa | ggtaggtact | ggcctccaag ctctgagata | 10860 |
| cacggccctg | ccctgggacc | aagggggtct | tggaggcttt | ctggtccagc tgtctggttg | 10920 |
| aacagatagg | gaaactgagg | cccagaggga | gggaggctta | aaagggacgc aagggacctg | 10980 |
| gcagaaatgg | ccacagggac | ccagcctctg | ctgcgttcag | ggccccgctg gtgcctgcgc | 11040 |
| cccaggccgg | ggctgatccc | atagagtggg | tgtgaacatg | tgccctaccc tcggatgggc | 11100 |
| aatgccctag | gaggatgggg | cctggaagcc | ccagccggag | cacagggtac aggctcgccc | 11160 |
| atggagggca | ccactggctt | ggggccacac | acccagcact | ggctcacgag ggtcctgggg | 11220 |
| agagctagaa | cagactggca | ctgcctggca | gggccccacg | ggagccactg actgtgttcc | 11280 |
| gtgtccgagt | cactgagtgg | cagatggcac | ctgcctcccg | gccacgggga tgaataagga | 11340 |
| aacgcacgta | aaagtagcgc | tgagtctcca | ggccccgctt | ctgtgatggg gtggggaaac | 11400 |
| cccagggcca | caggggctcc | gacccgcatc | aacccaccag | gcccctccat acacattggc | 11460 |
| ccccagcccT | tctctggggc | ttccactgag | ggggcccaggg | ccccacgct gcatggcagc | 11520 |
| cagcctgctc | tgcggcacag | accctccctc | caccatgagt | ctttttcccaa ggtgggttgg | 11580 |
| gagacctcag | ggaaggaggc | caggcacagg | ggtactgtgg | atgccaacac ctgcccccca | 11640 |
| tcaggagctg | atctcagtgc | actttggaga | ggacggcgcc | tcctacgagg cagaaatcag | 11700 |
| ggagctggag | gccctgcggc | aggtgtgtgg | ttcccccgcc | cacccaccct cctgcagccc | 11760 |

```
tgggagacac atgcagaggc tgaagctgaa gtcaggaaca gacagaggag ctcagcgtag   11820
acatctcgag gacgtgggga gacgggcgca ccaggggccc tgtgtgtcca gacccagcca   11880
gggggcgtgg agggctccc  aggtggctcc ggtgccgcat gctgctggcc ttcgggagtc   11940
acggctgccc agggccccac tggctttgcc tccccgcccc ccatggtgct ggtgcccatg   12000
ggacttccca gggcagtgtg tgtgagtggg gtgggccagg gcgtggggc  ccagtggctc   12060 ctgccctgca ggccatgcgg accccagcc  ggaatgagtc gggcctggag ctgctcacag   12120
cctattacaa ccagctgtgc ttcctggatg cgcgcttcct caccccctgcc aggagcctcg   12180 ggctcttctt ccactggtag gggctctgcg ggcggaggca ccctggggag gggaggccca   12240
gctgcgggaa ccgtgggaac tccacccagc ctgacccaac actgcaggta cgactcgctt   12300
actggggtcc cggcccagca gcgtgccctg gccttcgaga agggcagcgt tctcttcaac   12360
atcggtgccc tccacacgca gattggggcg cgccaggacc gctcctgcac cgagggtgcc   12420
cgccgcgcta tggaggcctt ccagagggcc gctggtgagg gcggcccggg ccgcggtggg   12480
gcacggcgcg gtgccaggt  gttgcagagc ccctttttgca gggcaggagc tggggagtgg   12540
ttaggacatc agtccctcag gtaggggag  tgagcacatc aggtccatat gtgtcccagg   12600
agcatcccta gctggccgcc ctgagtgctg catggggcag agatgggcag gtacagggcc   12660
ctgcctgtgt gagcacccct ccctccgcag gggccttcag cctcctgagg gagaacttct   12720
cccatgcgcc gagcccagac atgagcgctg cgtccctctg cgcactggag cagctcatga   12780
tggcccaggc ccaggaatgt gtgtttgagg gcctctcacc acctgcctcc atggcccccc   12840
aagactgcct ggcccagctg cgcctggcgc aggaggccgc ccaggtgagc tcgggcaccc   12900
gtgtcaggat gcagggggtg gggccgagct ggggtcagag cccaggtcca ggcatgcgtg   12960
agctctccca cctccttcct tgtgtgtcag ccccgagcca gctgttgtcc tgctccctgg   13020
gggggctggt caggaacctg ggacccgag  cctctgcctc caggggatgg cacaaagcag   13080
caggaactga ggtgccaggg aggctgctgg gatggtggtc ggagcaggtg gaggctgggt   13140
agggagaagc aggcaccacc tggagagtgg gaggccctcg cgtgcctgcc acatccaccg   13200
gcaggtggca gccgagtaca ggctagtgca ccggaccatg gcccagccac ccgtccacga   13260
ctacgtgcct gtctcctgga ctgccctggt gcatgtcaag gccgagtact tccgctccct   13320
ggcccactac cacgtagcca tggccctctg cgacggctcc cgtgagtgcc caccgcactt   13380
gcccatggta ctgccaaggc ccccccgcgc agggctcaca gcctctctgt cccccagcag   13440
cgaccgaggg agagctcccc acgcacgagc aggtcttcct gcagcccccc acctcctcta   13500
agccccgagg ccctgtgctg ccgcaggagc tggaggagcg caggcagctt ggtaaggcgc   13560
ccatgggtgg agtgccctgg ggctcagatg gtcaccaacg gtggcagggt gtcccccacc   13620
accctcatgc tgtttgccac ctgctgtccc cgtgctgacg agttgggcca cctacctatc   13680
cctggatggc ctgtgcctga tgggtgacgg cccagcgcag gggcccagg  agtgctgggc   13740 agcctctgag caggtgggag accactggga gcagctcatc cctggcccct gctttgcacg   13800
tggcagagcc ctcctgcaca gccagctcct caccccgtg  gcgcgcaccc caacgaaag   13860 tggctgtgat gagcccccaca gccctggcgt tgcccactcc ttctgccacg tcccagggcc   13920
cacgggccca catggtgtgt gacatcccag tgcccgcgt  gcaggcaagg cacacctgaa   13980
gcgtgccatc ctggggcagg aggaggcgct gcggctgcac gccctgtgcc gcgtcctgcg   14040
cgaggtggac ctgcttcggg ctgtgatctc ccagacgctg cagcgctcac tggccaagta   14100
```

-continued

```
tgcggagctc gaccgtgagg atgacttctg tgaggctgcc gaggcccggg acatccagcg      14160
tgagcagcca gggcctgtct gggtggctgc atccctggcc agggtggggg ccttcgtcct      14220
ggagaaaggg aggctgattg cattaaagat gcagtcacca cgatgaatta acagcagta      14280 gcactttcca ggccacgatc acagggaccc acagagctgc tgggcccttc aggggcctgg      14340
gggatgacca cgctcctcag cacctccctc cctgcactgg cctcctaccc tgaggggaag      14400
cccacagacc caggacaggc atggctggga cttcagggag ggattttggg agccacttgg      14460
ggcagagggg gctgtgtgtt cagggcacac ctggggcagc tcctcccacc attgcagagt      14520
ggccaggcct ggaggtcaga agcggggcct gtgtgcactc agggtcatgc cctgcgccct      14580
ggaaaatccc cgaggcaggt ctccacagtc tcccagctta gctctgctct tacaccctct      14640
cagctaagac ccaccagaag ccagaggcca ggatgccacg cctgtcccag gggaaggggc      14700
ctgacatctt ccatcggctg gtgagcacac ccgtccccag gcaccgccca gcatgggcag      14760
cttgggctgt gtggctctga ccagcacatg gcctcagaca ggccattgat ggtggtccag      14820
ccctccccac ccaccttgtg gaaccccacg gtgtccctcg gtgcacaggt tggatggatg      14880
tgctagtcag gtggggtctc ctcagtgtgt ggcccagctg ggcctctgac ctctgagccc      14940
ctgccagggg cccctgtctg tgttctcagc caagaaccgg tggcggctgg tggggcccgt      15000
ccacctgacc cgaggagagg gcggctttgg cctcacgctt cggggagact cgcctgtcct      15060
catcgctgcc gtcattccag ggagccaggc cgcggtaagg gccccgccgg cccctgagg      15120 ctgagtcctt ggtgccagcc agggtgtcct gtccccacct caccgtccaa gtctccccac      15180
aggcggctgg cctgaaggag ggcgactaca ttgtgtcagt gaatgggcag ccatgcaggt      15240
ggtggagaca cgcggaggtg gtgacggagc tgaaggctgc gggagaggcg ggcgccagcc      15300
tgcaggtggt gtcgctgctg cccagctcta gactgcccag cttggtgagc cctggggcc      15360 ccagaggggc ggtccccagc ttgctgtcac caccctggcc ctgggcctgc cttggatgct      15420
tgagcaacat tgggaagggg aggtggggct gcaggtaacc ctccctgggc cgcctcctgg      15480
gcaggggcca cctgtgctgt ggcctccatc tggcagctct tgccctgacc cgaggatgc      15540 tgcagcccac ccctcactgg gcctctgtat cctcagactg gaggcttctg ggccaggcgc      15600
tccatcccag aggttttctc tacccagcat ggctgaccca gggttgggtg aaacccatgg      15660
gcccctgcta tgtggccacc ctgatgggag cccccaaaca agcccccgac gtgccagccc      15720
ctcccaggtg gttctcaccc ctcccagact ggctgcaggt ggggacaggc cagcagtggc      15780
tgaccacagt ctgtctctgt ccctgctgca gggggaccgc cggcccgtcc tgctgggccc      15840
caggggcctt ctaaggagcc agagggagca tggttgcaag accccggcat ccacgtgggc      15900
cagtccccgg ccctcctca actggagccg aaaggcccag cagggcaaga ctggaggctg      15960 ccccagccc tgtgccccag tgaagccagc tccgccctca tccttgaagc acccagggtg      16020
gccgtgaggg ccaggatccc tgcacgcctc agccctggct ccagctggca gcaagcaccg      16080
agcatgccct cccacccag aggacctccg ggcaatgcct gtcccgcctc atgctggagg      16140
ctgcctcggg cacctgcctg cccattaaag actggtcaga cctgtctgag cccagtgatg      16200
ggagctgtgg cctcttcacc cacacacaga aggatgccag tccctctgtc ggtctgaggt      16260
cagcttcctg gggctgcccc acctgagggg ctccttacag ggtgctcctc acagccatcc      16320
catctgtacc cccgggctct gtccaccctg ctgctgccct gggcacagac cctgaggtct      16380
cagtcctgcc tccagccaag tttctgcctg gtgcccagtg attcctgctg ggcacccctt      16440
cgctcactgc ccctccacca tgcagcagcc agacacaccc acagcacccg aagacctcta      16500
```

```
ggccgggtcc cagacatggc cttcccccaa aatacttcct gctgtcctgt ctgtgcacag   16560
agcaagggac tccccacctc tgcgccctgt gctggtcatc atgggctctg tgctggtcaa   16620
cccagcaagt gtcccgtttg cccaggagtc cctggtgtcg tggcccaggt ctcatggtgg   16680
ccctaagcct gccagccctg ctgcccgcct tgctgtcctg ctctgagcat gggtgccacc   16740
ctccagctcc tgggcgtgtc acttctctct gagcctgggg cctgcatggg cccccagccc   16800
tccccagcct gcttgggccg ctcctgctgg cctccacagg ccgtgagctg tcagtgtctc   16860
aagcagggga agtgagggct gcctccaggc ctccgtgtac tgggtggaca atggccccca   16920
aaggccgtcg gcaagaacac cacctccagg acccctacag cagtgggctc aggacttggg   16980
caccaagagg agagggtggg aagggctgca gagtcagggc tgcacccaag aggagccacg   17040
gagccggagc cggagcggag gcccccaccg agggccccag gcctggcag gttccggaag   17100 agacagggcc agcgggagtc attccctgca gccactaggg ggcagccgcc acccgctcag   17160
cagccctggg aggcggcacg ggcaggtgcg ccttgggagg gctgaggcaa agaccccggg   17220
tagaaaggcg gccccccagct ctgcgagacc cctgccctct tgtccagtcc cttccgaggg   17280
tccgcaggtg agagcagcct gccctgcatc ccaggctctg gttccagggt ccagggccct   17340
gcgctgccac ctccctcgtg cttcagccaa gaaaatgggg gtgcaagtag ggtgtttggg   17400
gtcccagaga cgcaggcgcc gcggcgcgat cttcctgggc aggagggcag ggctccccaa   17460
cctgcctgag ccggggtggg ggtccaggtc ccccacttgc ccttgtggga aaatccctgt   17520
ctcagcagaa tgggccaagg tcacgcaggt ctccccagca cgtgttaatt tggttaataa   17580
aactgtggat caaggaggcc agtaggcact aactggggat gacagggtgg cagccctgtc   17640
tgggaagtgc agggactccc cacctcctgt ggcctgtcga gacccaagct ggggacagag   17700
ctgccacctg cctcctgcat ggtgggcgcc aggccaccat agcctggggg aggggctttt   17760
tgcccagaga gcacgcctct ccccaccgca gacccctggg gtgcgcccaa cccgtcccac   17820
ccctgcccac acatgcctct cccctggctg ccaccaagcc tgggcctgtg ctcctggccc   17880
tgccctctgc cccaggccat tcctccccct gctgcccccc ccccgccgt cgtgtccctc   17940 tgccacagag gggggcctc acagctgaag ccacacgtgg ctgggacctg ctcccgtca   18000 ccgcctccgt cctgtgaagt ggaggaagcc tggtgcacag gggtgctgtg gcgatgtggg   18060
gggccctgag gtcctgctgc cagccagggg gagggggcg gaggtcctgg gatctggggt   18120
ccagagttct agtcaaggca gggctgggca ggagggggggt cccctcccc accttccact   18180 tggggctgct ctccagaaga gaaagcggat gcctaccagc ccagccctc agacttggac   18240 catgcccctc cggcatctgt gggagtcctg ccagacagcc cctgggctgc gggaagggac   18300
cgcgccccat cccatcctca tccctgcagt agctggtggc tgcctgcccg gcgcaggggc   18360
ctgctgaaca ggggactgcc ctgtccagcc cacccacggg actccaagtc cacacaggca   18420
gcagagtcgg cagcggtggg cagagtgggg gggcatcacc atggctcctc agggactggt   18480
caagggtgtg atgcctggcc tggcaggacc tgcagtttca cccccggggc cagctgtggc   18540
ctgtgccccg ccagagggca gtgcagcccc tggggccagc acacaggagg cggcagctca   18600
gggtcctgtc ccatctgccc aggctaggga gcaaagcagg atcagggcga ggctgcgagg   18660
ctgggggaag gcagggctgg ccgctgggga gcgctcggtc cgcaggctgt gcggtgagag   18720
ccactgggtg aggcttcccg gggggcacag ctgcccgag gggccggctc aaggctgtcc   18780
ctgcagcagc acgtgttggt gcttgcctgc cccccccgca gcgccacacc gcggcctctg   18840
```

```
tggagcccgt tctcttccct tgaagtcctg cttgcgcact cctgggcgtt tctggctagc   18900
acctttttgg cttttaggga cgggttagtg tcccttcctc agatggcccg gcctggacac   18960
accccatgca tgggccttag ccccactttt ctgggccagc cttatcactt tgggcactgt   19020
gtcac                                                                19025
```

<210> SEQ ID NO 4
<211> LENGTH: 634
<212> TYPE: PRT
<213> ORGANISM: Mus musculus

<400> SEQUENCE: 4

```
Met Ile Leu Glu Glu Arg Pro Asp Gly Gln Gly Thr Gly Gly Glu Ser
 1               5                  10                  15

Ser Arg Pro Gln Asp Asp Gly Ser Ile Arg Lys Gly Tyr Gly Ser Phe
                20                  25                  30

Val Gln Asn Gln Pro Gly Gln Leu Gln Ser His Arg Ala Arg Leu His
            35                  40                  45

Gln Gln Ile Ser Lys Glu Leu Arg Met Arg Thr Gly Ala Glu Asn Leu
        50                  55                  60

Tyr Arg Ala Thr Ser Asn Thr Trp Val Arg Glu Thr Val Ala Leu Glu
65                  70                  75                  80

Leu Ser Tyr Val Asn Ser Asn Leu Gln Leu Leu Lys Glu Glu Leu Ala
                85                  90                  95

Glu Leu Ser Thr Ser Val Asp Val Asp Gln Pro Glu Gly Glu Gly Ile
            100                 105                 110

Thr Ile Pro Met Ile Pro Leu Gly Leu Lys Glu Thr Lys Glu Leu Asp
        115                 120                 125

Trp Ala Thr Pro Leu Lys Glu Leu Ile Ser Glu His Phe Gly Glu Asp
    130                 135                 140

Gly Thr Ser Phe Glu Thr Glu Ile Gln Glu Leu Glu Asp Leu Arg Gln
145                 150                 155                 160

Ala Thr Arg Thr Pro Ser Arg Asp Glu Ala Gly Leu Asp Leu Leu Ala
                165                 170                 175

Ala Tyr Tyr Ser Gln Leu Cys Phe Leu Asp Ala Arg Phe Phe Ser Pro
            180                 185                 190

Ser Arg Ser Pro Gly Leu Leu Phe His Trp Tyr Asp Ser Leu Thr Gly
        195                 200                 205

Val Pro Ala Gln Gln Arg Ala Leu Ala Phe Glu Lys Gly Ser Val Leu
    210                 215                 220

Phe Asn Ile Gly Ala Leu His Thr Gln Ile Gly Ala Arg Gln Asp Cys
225                 230                 235                 240

Ser Cys Thr Glu Gly Thr Asn His Ala Ala Glu Ala Phe Gln Arg Ala
                245                 250                 255

Ala Gly Ala Phe Arg Leu Leu Arg Glu Asn Phe Ser His Ala Pro Ser
            260                 265                 270

Pro Asp Met Ser Ala Ala Ser Leu Ser Met Leu Glu Gln Leu Met Ile
        275                 280                 285

Ala Gln Ala Gln Glu Cys Ile Phe Lys Gly Leu Leu Leu Pro Ala Ser
    290                 295                 300

Ala Thr Pro Asp Ile Cys Pro Asp Gln Leu Gln Leu Ala Gln Glu Ala
305                 310                 315                 320

Ala Gln Val Ala Thr Glu Tyr Gly Leu Val His Arg Ala Met Ala Gln
                325                 330                 335
```

-continued

```
Pro Pro Val Arg Asp Tyr Leu Pro Ala Ser Trp Thr Asn Leu Ala His
        340             345             350

Val Lys Ala Glu His Phe Cys Ala Leu Ala His Tyr His Ala Ala Met
        355             360             365

Ala Leu Cys Glu Ser His Pro Ala Lys Gly Glu Leu Ala Arg Gln Glu
        370             375             380

His Val Phe Gln Pro Ser Thr Pro His Glu Pro Leu Gly Pro Thr Leu
385             390             395             400

Pro Gln His Pro Glu Asp Arg Arg Lys Leu Ala Lys Ala His Leu Lys
        405             410             415

Arg Ala Ile Leu Gly Gln Glu Ala Leu Arg Leu His Thr Leu Cys
        420             425             430

Arg Val Leu Arg Lys Val Asp Leu Leu Gln Val Val Val Thr Gln Ala
        435             440             445

Leu Arg Arg Ser Leu Ala Lys Tyr Ser Gln Leu Glu Arg Glu Asp Asp
    450             455             460

Phe Phe Glu Ala Thr Glu Ala Pro Asp Ile Gln Pro Lys Thr His Gln
465             470             475             480

Thr Pro Glu Gly Pro Leu Ser Val Phe Ser Thr Lys Asn Arg Trp Gln
            485             490             495

Leu Val Gly Pro Val His Met Thr Arg Gly Glu Gly Gly Phe Gly Phe
            500             505             510

Thr Leu Arg Gly Asp Ser Pro Val Leu Ile Ala Ala Val Val Pro Gly
        515             520             525

Gly Gln Ala Glu Ser Ala Gly Leu Lys Glu Gly Asp Tyr Ile Val Ser
    530             535             540

Val Asn Gly Gln Pro Cys Lys Trp Trp Lys His Leu Glu Val Val Thr
545             550             555             560

Gln Leu Arg Ser Met Gly Glu Glu Gly Val Ser Leu Gln Val Val Ser
            565             570             575

Leu Leu Pro Ser Pro Glu Pro Arg Gly Thr Gly Pro Arg Arg Ala Ala
            580             585             590

Leu Leu Trp Asn Gln Arg Glu Cys Gly Phe Glu Thr Pro Met Pro Thr
        595             600             605

Arg Thr Arg Pro Trp Pro Ile Leu Gly Trp Ser Arg Lys Asn Lys Gln
    610             615             620

Gly Lys Thr Gly Ser His Pro Asp Pro Cys
625             630
```

ISOLATED HUMAN KINASE PROTEINS, NUCLEIC ACID MOLECULES ENCODING HUMAN KINASE PROTEINS, AND USES THEREOF

RELATED APPLICATIONS

The present application is a Continuation-In-Part application of U.S. Ser. No. (09/773,371), filed Feb. 1, 2001 now abandoned.

FIELD OF THE INVENTION

The present invention is in the field of kinase proteins that are related to the protein kinase N (PKN) subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION
Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation; is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, est.), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol 1:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (L-1).

PRK (proliferation-related kinase) is a serum/cytokine inducible STK that is involved in regulation of the cell cycle and cell proliferation in human megakaroytic cells (Li, B. et al. (1 996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks NK (1992) *Annu. Rev. Cell. Biol.* 8:463–93). Regulation of PTK activity may therefore be an important strategy in controlling some types of cancer.

Protein Kinase N (PKN) and PKN-related Protein Rhophilin

The novel human kinase protein, and encoding gene, provided by the present invention is related to the family of protein kinase N (PKN) proteins and the PKN-related protein, rhophilin. Both of these proteins are serine-threonine protein kinase that bind to, and activate, rho guanosine 5'-triphosphatase (rho GTPase), and thus may also be referred to as GTP-rho binding proteins. As used herein, "protein kinase N" encompasses protein kinase N (PKN) proteins, rhodophilin, GTP-rho-binding proteins, and serine/threonine protein kinases. Rhophilin and PKN share 40% sequence identity in a region of the amino terminus, and this is the site for rho binding (Watanabe et al., *Science* Feb. 2, 1996; 271(5249):645–8). The human protein of the present invention shows a particularly high degree of similarity to mouse GTP-rho binding protein 1.

Rho GTPase is important for regulating cell adhesion and cytokinesis, and is particularly important for the assembly and reorganization of focal adhesions and actin stress fibers in fibroblasts in response to growth factors (Ridley et al., *Cell* Aug. 7, 1992; 70(3):389–99). Therefore, GTP-rho binding proteins such as PKN, rhodopsin, and the novel human protein/gene of the present invention may be useful for regulating various aspects of cell adhesion and cytokinesis through their interaction with Rho GTPase.

Kinase proteins, particularly members of the protein kinase N subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the protein kinase N subfamily.

SUMMARY OF THE INVENTION

The present invention is based in part on the identification of amino acid sequences of human kinase peptides and proteins that are related to the protein kinase N subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes.

DESCRIPTION OF THE FIGURE SHEETS

FIG. 1 provides the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes.

FIG. 2 provides the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. The gene encoding the novel kinase protein of the present invention is located on a genome component that has been mapped to human chromosome 8 (as indicated in FIG. 3), which is supported by multiple lines of evidence, such as STS and BAC map data.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the protein kinase N subfamily. Utilizing these sequences, additional genomic sequences were assembled and transcript and/or cDNA sequences were isolated and characterized. Based on this analysis, the present invention provides amino acid sequences of human kinase peptides and proteins that are related to the protein kinase N subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the protein kinase N subfamily and the expression pattern observed. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known protein kinase N family or subfamily of kinase proteins.

Specific Embodiments
Peptide Molecules

The present invention provides nucleic acid sequences that encode protein molecules that have been identified as being members of the kinase family of proteins and are related to the protein kinase N subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS; 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 8 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene encoding the novel kinase protein of the present invention is located on a genome component that has been mapped to human chromosome 8 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more filly described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–130 (1990).

Variant kinase peptides can be fully functional or can lack function in one or more activities e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation,ihydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, and uterus endometrial adenocarcinomas, as indicated by virtual northern blot analysis. In addition, PCR-based tissue screening panels indicate expression in human leukocytes. A large percentage of pharmaceutical agents are being developed that modulate the activity of kinase proteins, particularly members of the protein kinase N subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes. Such uses can readily be determined using the information provided herein, that which is known in the art, and routine experimentation.

The proteins of the present invention (including variants and fragments that may have been disclosed prior to the present invention) are useful for biological assays related to kinases that are related to members of the protein kinase N subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, and uterus endometrial adenocarcinomas, as indicated by virtual northern blot analysis. In addition, PCR-based tissue screening panels indicate expression in human leukocytes.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normnally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, and uterus endometrial adenocarcinomas, as indicated by virtual northern blot analysis. In addition, PCR-based tissue screening panels indicate expression in human leukocytes.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in eye retinoblastomas, placenta choriocarcinomas, germ cells, bocio tumors, pre-B cell acute lymphoblastic leukemias, Wiln's tumors of the kidney, uterus tumors, brain anaplastic oligodendromas, uterus endometrial adenocarcinomas, and leukocytes. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fuised to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and.methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharnacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more, or less active in substrate.binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab'))$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinasebinding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylarnine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, and uterus endometrial adenocarcinomas, as indicated by virtual northern blot analysis. In addition, PCR-based tissue screening panels indicate expression in human leukocytes. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 8 (as indicated in FIG. 3), which is supported by multiple lines of evidence, such as STS and BAC map data.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel kinase protein of the present invention is located on a genome component that has been mapped to human chromosome 8 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, and uterus endometrial adenocarcinomas, as indicated by virtual northern blot analysis. In addition, PCR-based tissue screening panels indicate expression in human leukocytes. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, and uterus endometrial adenocarcinomas, as indicated by virtual northern blot analysis. In addition, PCR-based tissue screening panels indicate expression in human leukocytes.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, and uterus endometrial adenocarcinomas, as indicated by virtual northern blot analysis. In addition, PCR-based tissue screening panels indicate expression in human leukocytes. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, uterus endometrial adenocarcinomas, and leukocytes.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. The gene encoding the novel kinase protein of the present invention is located on a genome component that has been mapped to human chromosome 8 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et. al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule. is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other finctional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in humans in eye retinoblastomas, placenta choriocarcinomas, germ cells, bocio tumors, pre-B cell acute lymphoblastic leukemias, Wilm's tumors of the kidney, uterus tumors, brain anaplastic oligodendromas, and uterus endometrial adenocarcinomas, as indicated by virtual northern blot analysis. In addition, PCR-based tissue screening panels indicate expression in human leukocytes. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonticleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence infonnation disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can finction in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by micro injection, retroviral infection, and allowing the oocyte to develop in a pseudo pregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (992). Another example of a recombinase system is the FLP recombinase system of *S. cerevisiae*(O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudo pregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
    (a) a nucleotide sequence that encodes a polypeptide comprising the amino acid sequence of SEQ ID NO:2;
    (b) a nucleotide sequence consisting of SEQ ID NO:1;
    (c) a nucleotide sequence consisting of SEQ ID NO:3; and
    (d) a nucleotide sequence that is completely complementary to a nucleotide sequence of (a)–(c).

2. A nucleic acid vector comprising the nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide.

5. An isolated polynucleotide consisting of the nucleotide sequence set forth in SEQ ID NO:1.

6. An isolated polynucleotide consisting of the nucleotide sequence set forth in SEQ ID NO:3.

7. A vector according to claim 2, wherein said vector is selected from the group consisting of a plasmid, a virus, and a bacteriophage.

8. A vector according to claim 2, wherein said isolated nucleic acid molecule is inserted into said vector in proper orientation and correct reading frame such that a polypeptide comprising SEQ ID NO:2 may be expressed by a cell transformed with said vector.

9. A vector according to claim 8, wherein said isolated nucleic acid molecule is operatively linked to a promoter sequence.

* * * * *